(12) United States Patent
Broeckx et al.

(10) Patent No.: US 10,801,014 B2
(45) Date of Patent: Oct. 13, 2020

(54) METHOD AND COMPOSITION FOR INDUCING CHONDROGENESIS OR TENOGENESIS IN MESENCHYMAL STEM CELLS

(71) Applicant: GLOBAL STEM CELL TECHNOLOGY, Evergem (BE)

(72) Inventors: Sarah Yolande Kristel Broeckx, Bocholt (BE); Jan Hilda Marie Jozef Spaas, Bocholt (BE)

(73) Assignee: Global Stem Cell Technology, Evergem (BE)

( * ) Notice: Subject to any disclaimer, the term of this patent is extended or adjusted under 35 U.S.C. 154(b) by 298 days.

(21) Appl. No.: 15/038,172

(22) PCT Filed: Dec. 6, 2013

(86) PCT No.: PCT/EP2013/075782
§ 371 (c)(1),
(2) Date: May 20, 2016

(87) PCT Pub. No.: WO2015/082014
PCT Pub. Date: Jun. 11, 2015

(65) Prior Publication Data
US 2016/0289639 A1 Oct. 6, 2016

(51) Int. Cl.
*C12N 5/077* (2010.01)
*C12N 5/0775* (2010.01)

(52) U.S. Cl.
CPC .......... *C12N 5/0655* (2013.01); *C12N 5/066* (2013.01); *C12N 5/0663* (2013.01); *C12N 5/0665* (2013.01); *C12N 5/0668* (2013.01); *C12N 2501/105* (2013.01); *C12N 2501/115* (2013.01); *C12N 2501/15* (2013.01); *C12N 2502/137* (2013.01); *C12N 2502/1352* (2013.01); *C12N 2502/1358* (2013.01); *C12N 2502/1382* (2013.01)

(58) Field of Classification Search
CPC ............ C12N 5/066; C12N 2506/1346; C12N 2506/1369; C12N 2501/15
See application file for complete search history.

(56) References Cited

FOREIGN PATENT DOCUMENTS

WO    WO 2013/165252 A1    11/2013

OTHER PUBLICATIONS

Hankemeier et al., Modulation of proliferation and differentiation of human bone marrow stromal cells by fibroblast growth factor 2: Potential implications for tissue engineering of tendons and ligaments. Tissue Engineering, vol. 11, No. 1/2 (2005) pp. 41-49., (Year: 2005).*
R. Ian Freshney, "Quantitation." In: Culture of Animal Cell: A Manual of Basic Technique and Specialized Applications. (Hoboken, NJ, John Wiley & Sons, Inc., 2010), pp. 335-364. QH585.2.F74 2010. (Year: 2010).*
Durgam, S., In vitro comparison of equine tendon- and bone marrow-derived cells expanded with FGF-2 prior to culturing with tendon matrix and IGF-I. Thesis. University of Illinois, 2010 [retrieved on Jun. 19, 2018]<URL:https://pdfs.semanticscholar.org/ebdb/7f5ae8808512973509d735d6dd1052694998.pdf>. (Year: 2010).*
Wagner et al., Comparative characteristics of mesenchymal stem cells from human bone marrow, adipose tissue, and umbilical cord blood. Experimental Hematology, vol. 33 (2005) pp. 1402-1416. (Year: 2005).*
Fu et al., Comparative study of the biological characteristics of mesenchymal stem cells from bone marrow and peripheral blood of rats. Tissue Engineering Part A, vol. 18, No. 17-18 (online Jul. 30, 2012) pp. 1793-1803. (Year: 2012).*
NG et al., "PDGF, TGF-β, and FGF signaling is important for differentiation and growth of mesenchymal stem cells (MSCs): transcriptional profiling can identify markers and signaling pathways important in differentiation of MSCs into adipogenic, chondrogenic, and osteogenic lineages," *Blood*, American Society of Hematology, vol. 112(2), pp. 295-307 (Jul. 15, 2008).
Ronziere et al., "Chondrogenic potential of bone marrow- and adipose tissue-derived adult human mesenchymal stem cells," *Bio-Medical Materials and Engineering*, Kyoto University, Japan, vol. 20(34), pp. 145-158 (2010).
Spaas et al., "Culture and characterisation of equine peripheral blood mesenchymal stroma cells," *Veterinary Journal*, vol. 195(1), pp. 107-113 (Jan. 2013).
Tsai et al., "Regulation of mesenchymal stem cell chondrogenesis by glucose through protein kinase C/transforming growth factor signaling," *Osteoarthritis and Cartilage / OARS*, Osteoarthritis Research Society Feb. 2013, vol. 21(2), pp. 368-376 (Feb. 2013).

* cited by examiner

*Primary Examiner* — Kara D Johnson
(74) *Attorney, Agent, or Firm* — Hodgson Russ LLP

(57) ABSTRACT

The current invention concerns a cell medium for in vitro inducing chondrogenesis or tenogenesis in mesenchymal stem cells (MSCs). The medium includes a glucose medium supplemented with at least one growth factor. The growth factor is selected from fibroblast growth factors (FGF) or transforming growth factors (TGF). FGF or TGF is present in a total concentration of between 1 and 15 ng/ml. In both cases, IGF can be added to enhance the induction process. In a further aspect, the invention provides for a use of such cell medium as well as a method for inducing isolated mesenchymal stem cells (MSCs) and a cell composition obtained by such method.

8 Claims, 17 Drawing Sheets

METHOD AND COMPOSITION FOR INDUCING CHONDROGENESIS OR TENOGENESIS IN MESENCHYMAL STEM CELLS

CROSS-REFERENCE TO RELATED APPLICATIONS

This application is the U.S. National Phase under 35 U.S.C. § 371 of International Application PCT/EP2013/075782, filed Dec. 6, 2013.

TECHNICAL FIELD

The present invention relates to the field of methods and compositions for directing mesenchymal progenitor cells cultivated in vitro to differentiate into specific cell lineage pathways, and particularly to such directed lineage induction prior to, or at the time of, their implantation into a recipient or host for the therapeutic treatment of pathologic conditions in humans and other species.

BACKGROUND

Mesenchymal stem cells (MSCs) are the formative pluripotent blast or embryonic-like cells found in bone marrow, blood, dermis, and periosteum that are capable of differentiating into specific types of mesenchymal or connective tissues including adipose, osseous, cartilaginous, elastic, muscular, and fibrous connective tissues. The specific differentiation pathway which these cells enter depends upon various influences from mechanical influences and/or endogenous bioactive factors, such as growth factors, cytokines, and/or local micro-environmental conditions established by host tissues.

Damage to the articular surfaces of synovial joints, or tendon and ligament lesions can arise from trauma, from diseases (e.g. osteoarthritis), and as a result of the aging process. To date, most prescribed therapies include conservative treatments such as administration of NSAIDs, corticoid treatment, surgical treatments, bandaging, etc. However, the latter are often found to be ineffective and time-consuming.

It has been proposed that treatment of damage to chondrogenic and tenogenic tissue could be repaired by implanting autologous cells (e.g. tenocytes or chondrocytes). Articular cartilage for instance is created and maintained during prenatal and postnatal growth by mesenchymal cells that have differentiated into articular chondrocytes. Individuals may lose the ability to repair major synovial defects as they mature because their joints lack sufficient numbers of properly-differentiated cells to regenerate articular cartilage. Thus, there has been a great deal of interest in the hypothesis that damaged joint surfaces may be repaired by implanting autologous cells that will reconstitute a suitable extracellular matrix.

WO 1998 032 333 describes a process for producing chondrocytes from mesenchymal stem cells thereby using of a medium supplemented with growth factors from the transforming growth factor-β super-family.

WO 2010 007 551 discloses a method for inducing tenogenesis whereby a cell medium comprising bon morphogenetic proteins.

Although the autologous approach is promising, a recurrent problem in the art is the poor quality and compatibility of the cells used, hence leading to poor regenerative results and ineffective treatment. Often this is due to poorly induced or differentiated cells, which on its turn is a direct cause of an inadequate inducing methodology and inducing medium.

Thus, there is a continuing need for improved inducing methodology of stem cells towards tenocytes and chondrocytes, which can be used for regenerative therapy.

SUMMARY OF THE INVENTION

The present invention provides for a cell medium and use of such cell medium for inducing chondrogenesis or tenogenesis. The current invention furthermore relates to a method for inducing chondrogenesis or tenogenesis in isolated mesenchymal stem cells (MSCs) and a composition. Further embodiments of the invention are described herein.

The cell medium and methodology according to the current invention provides for an optimized manner of inducing tenogenesis or chondrogenesis in stem cells, obtaining a higher percentage of correctly induced cells. Furthermore, the cells according to the current invention are suitable for application in regenerative treatment.

DETAILED DESCRIPTION OF THE INVENTION

Figure 1A:
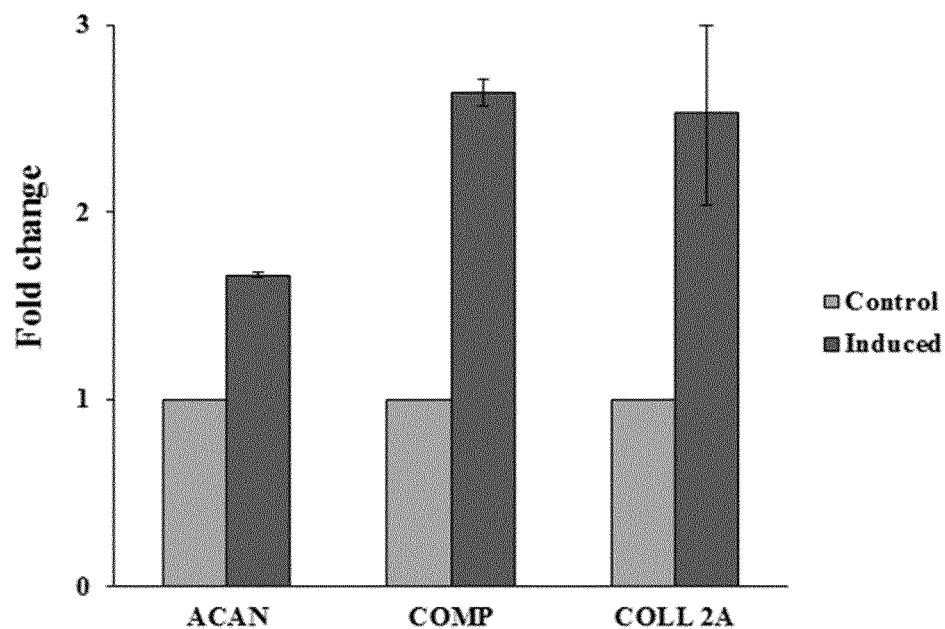
FIG. 1 shows marker expression of chondrogenic specific markers in chondrogenic induced MSCs according to the current invention (FIG. 1A).
FIG. 1B shows induction of tenogenic specific markers in tenogenic induced MSCs.

The present invention concerns a medium and method for inducing chondrogenesis and tenogenesis in mesenchymal stem cells. It was found by the inventors that by carefully selecting the growth factors in the inducing medium as well as by the concentration range and induction time, the induction phase is made far more efficient, and the quality of the obtained induced or differentiated cells is optimised compared to cells obtained by other methodologies. Moreover, the percentage of induced cells on a total population of mesenchymal stem cells is overall higher than compared to cells obtained by the methods currently known in the art. Finally, induction of stem cells towards cell or lineage specific cells generally results in great amount of cell death or apoptosis. The latter is reduced by making use of the cell medium and methodologies according to the current invention.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise," "comprising," and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The recitation of numerical ranges by endpoints includes all numbers and fractions subsumed within that range, as well as the recited endpoints.

The expression "% by weight" (weight percent), here and throughout the description unless otherwise defined, refers to the relative weight of the respective component based on the overall weight of the formulation.

In a first aspect, the invention provides a cell medium for in vitro inducing chondrogenesis or tenogenesis in mesenchymal stem cells (MSCs).

The term "inducing or induced" is to be understood as the process of activation of cell type specific genes or molecules in a multipotent or pluripotent cell, thereby driving such cell towards a more defined, specialized or differentiated cell lineage or cell type.

The term "chondrogenic differentiation/induction or chondrogenesis", as used herein, refers to the differentiation of or induction towards pluripotent or multipotent cells into cells producing an extracellular matrix close to that of cartilage or to cartilage cells. The chondrogenic differentiation/induction of pluripotent or multipotent cells is typically evaluated by the measurement of the pellet volume, cell morphology and matrix composition by hematoxylin-eosin (HE), safran and alcian blue staining.

The term "tenogenesis or tendogenic differentiation/induction" is to be understood as the differentiation of or induction towards pluripotent or multipotent cells into tendon or ligament fibroblasts or cells close to tendon or ligament fibroblasts.

For the purpose of the current invention, said tenocytes are to be defined as elongated fibroblast-like cells. Their cytoplasm is stretched between the collagen fibers. They are responsible for synthesis and turnover of tendon fibers and extracellular matrix.

For the purpose of the current invention, said chondrocytes are to be defined as cells that produce and maintain the cartilaginous matrix, which consists mainly of collagen and proteoglycans.

The term "pluripotent cells", as used herein, refers to undifferentiated cells which can give rise to a variety of different cell lineages of the three germ layers (endoderm, mesoderm and ectoderm).

The terms "multipotent cells" and "progenitor cells" are used herein interchangeably. They refer to undifferentiated cells which can give rise to a limited number of different cell lineages, including chondrocytes. Typical multipotent cells according to the invention are mesenchymal stem cells.

The term "mesenchymal stem cells" is to be understood as multipotent stromal cells derived or isolated from a principally mesenchymal or from stromal cells. Said mesenchymal stem cells are able to differentiate into various cell types, including but not limiting to osteoblasts, chondrocytes, tenocytes and adipocytes.

By preference, said inducing medium comprises a glucose medium supplemented with at least one growth factor, said growth factor is chosen from the group of fibroblast growth factors (FGF) or the group of transforming growth factors (TGF). In a preferred embodiment, said FGF or TGF is present in a total concentration of between 1 and 15 ng/ml. Outside these ranges, it was found that the induction and/or differentiation did not result in satisfying results, e.g. in view of obtained percentage of viable, healthy cells, which are suitable for downstream application such as regenerative therapies.

Whilst generally higher concentrations of growth factors are chosen in the art, the inventors have found that for the specific purpose of inducing chondrogenesis or tenogenesis in mesenchymal stem cells, a specific range of between 1 to 15 ng/ml of either a TGF or an FGF is sufficient and necessary for adequate induction and differentiation of these cells. More by preference, said growth factors are present in a total concentration of between 2 and 10 ng/ml, more preferably between 3.5 and 5.5 ng/ml.

In a further embodiment, said FGF is chosen from the group of FGF-1, FGF-2, FGF-3, FGF-4, FGF-5, FGF-6, FGF-7, FGF-8, FGF-9, FGF-10 or any combination thereof. Most preferably, said FGF is FGF-2.

In another embodiment, said TGF is chosen from the group of TGFα, TGFβ1, TGFβ2, TGFβ3 or any combination thereof. Most preferably, said TGF is TGF β3. By preference, said TGF concentration can vary between 2 and 10 ng/ml, more preferably between 2 and 8 ng/ml, more preferably between 3.5 and 5.5 ng/ml.

The cell medium of the current invention may further also be supplemented with other growth factors which may provide a supporting role for the tenogenic or chondrogenic induction and/or differentiation process. By preference, said medium may further comprise a growth factor chosen from the group of insuline-like growth factors (IGF). More by preference, said IGF is chosen from the group of IGF-1, IGF-2, IGF-I or any combination thereof. Most preferably, said IGF is IGF-I.

In a preferred embodiment, said IGF is present in a concentration of between 10 and 225 ng/ml, more preferably between 60 and 200 ng/ml.

Presence of one or more of the growth factors as described above, in their specific concentration range, are crucial for the inducing or differentiation process.

Said cell medium also comprises a glucose medium. Glucose is a necessary energy source for the cells. Energy derived from glucose is stored in the form of high-energy phosphate bonds in ATP, or other nucleotide triphosphates, and as energy-rich hydrogen atoms associated with the co-enzymes NADP and NAD. By preference, said glucose is D-glucose. In a further embodiment, said concentration of the glucose in the glucose medium will preferably range from 1 g/L to as high as 4.5 g/L.

Said glucose medium may be any culture medium known in the art which can be supplemented with glucose, such as, but not limiting to: Ames' Medium; Basal Medium Eagle (BME); BGJb Medium Fitton-Jackson Modification; Click's Medium; CMRL-1066 Medium; Dulbecco's Modified Eagle's Medium (DMEM); DMEM/Ham's Nutrient Mixture F-12 (50:50); F-12 Coon's Modification; Fischer's Medium; H-Y Medium (Hybri-Max®); Iscove's Modified Dulbecco's Medium (IMDM); McCoy's 5A Modified Medium; MCDB Media; Medium 199; Minimum Essential Medium Eagle (EMEM); NCTC Medium; Nutrient Mixture, Ham's F-10; Nutrient Mixture, Ham's F-12; Nutrient Mixture Ham's F-12 Kaighn's Modification (F12K); RPMI-1640; Serum-Free/Protein Free Hybridoma Medium; Waymouth Medium MB; Williams Medium E and various proprietary media.

The cell medium according to the current invention is further also supplemented with serum, preferably fetal serum such as fetal bovine serum or fetal calf serum (FBS or FCS). By preference, said serum is present in between 10% and 30% of the total volume of the cell medium. The current concentration was found to be important for the conservation of the stability the growth factor(s) in the medium.

The cell medium may furthermore be supplemented with antibiotics and/or antimycotics, such as penicillin and/or streptomycin, or any other suitable antibiotic or antimycotic for inhibition and prohibition of the growth of bacteria, fungi and/or yeast.

In a further aspect, the current invention also relates to the use of above described cell medium for inducing tenogenesis in isolated MSCs. By preference, said medium comprises a glucose medium, supplemented with an FGF chosen from the group of FGF-1, FGF-2, FGF-3, FGF-4, FGF-5, FGF-6, FGF-7, FGF-8, FGF-9, FGF-10 or a combination thereof, at a concentration of 5 to 10 ng/ml. Most preferably, said growth factor is FGF-2. In a further preferred embodiment, said medium comprises 8 ng/ml FGF-2. In another preferred embodiment, said medium comprises 5 ng/ml FGF-2.

In a third aspect, said current invention is related to the use of above described cell medium for inducing chondrogenesis in isolated MSCs. By preference, such medium comprises a glucose medium, supplemented with a TGF chosen from the group of TGFα, TGFβ1, TGFβ2, TGFβ3 or any combination thereof, at a concentration of 5 to 10 ng/ml. In a further embodiment, said glucose medium comprises an IGF chosen from the group of IGF-1, IGF-2, IGF-I or any combination thereof, at a concentration between 10 and 225 ng/ml. By preference, the used TGF is TGFβ3, whereas the used IGF is IGF-I. In a most preferred embodiment, said medium comprises 4 ng/ml TGFβ3 and 120 ng/ml IGF-I.

In a fourth aspect, the current invention also relates to a method for obtaining chondrocytes or tenocytes from isolated mesenchymal stem cells (MSCs). Said method comprises the step of culturing said MSCs in an inducing cell medium. Said inducing cell medium comprises a glucose medium supplemented with at least one growth factor, said growth factor is chosen from the group of Fibroblast Growth Factors (FGF) comprising FGF-1, FGF-2, FGF-3, FGF-4, FGF-5, FGF-6, FGF-7, FGF-8, FGF-9, FGF-10 or any combination thereof or chosen from the group of Transforming Growth Factors (TGF) TGFα, TGFβ1, TGFβ2, TGFβ3, or any combination thereof. In a preferred embodiment, said FGF or TGF is present in a total concentration of between 1 and 15 ng/ml in said medium, more preferably between 2 and 10 ng/ml.

In a further embodiment, said medium further comprises IGF, chosen from the group of IGF-1, IGF-2, IGF-I or any combination thereof. By preference, said medium comprises IGF-I, preferably at a concentration between 10 and 225 ng/ml, more preferably between 50 and 225 ng/ml, even more preferably between 60 and 200 ng/ml.

The isolated MSCs are seeded at a density of 2 to $30\times10^3$ MSCs/cm$^2$, more preferably between 6 to $14\times10^3$ MSCs/cm$^2$ in a medium as described above. Cell concentration was found crucial, as too densely seeded cells tended to show heavy cell death during induction, whereas too low density results in poorly induced cells and higher risk of mutations.

By preference, said cells are cultured for a period of 1-7 days, more preferably 12 to 72 hours in the inducing medium. The inventors have found that induction of cell or lineage-specific gene expression is detected within a time frame of 1 to 36 hours, from the start of the induction. The latter inducing rate differs greatly from what is known in the art. Generally, the first signs of induction of stem cells towards cell or lineage cells are seen within a far larger time span.

The induction of the cells may be followed by screening for molecular markers which are prerequisite for the specific nature of the cell lineage.

Figure 13:
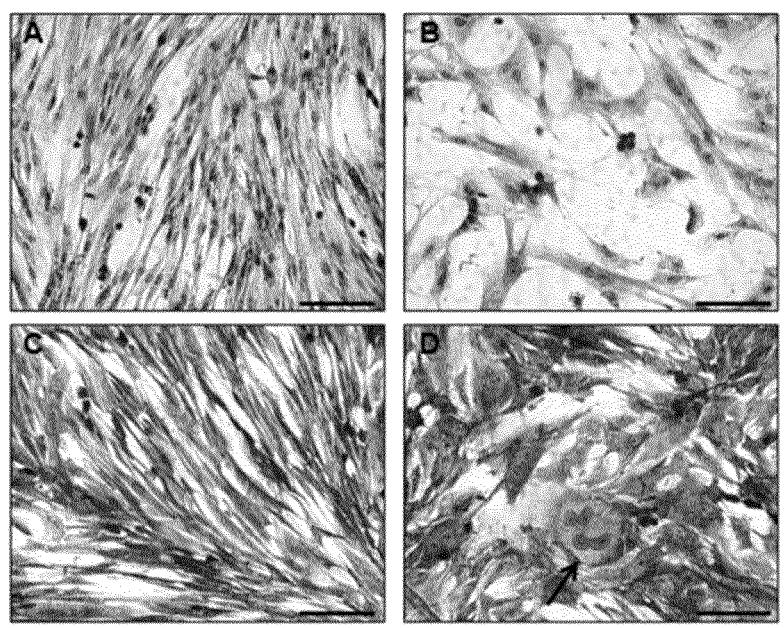
FIG. 13 shows representative images of peripheral blood (PB)-derived mesenchymal stem cells (MSCs) in their undifferentiated state (FIGS. 13A & C) and chondrogenic induced according to an embodiment of the current invention (FIGS. 13B & D) after Hematoxylin (FIGS. 13A & B) and Crystal Violet (FIGS. 13C & D) stainings. The typical chondrogenic morphology and lacune formation (black arrow) can be noticed after induction. Scale bars represent 50 μm.
Figure 14:
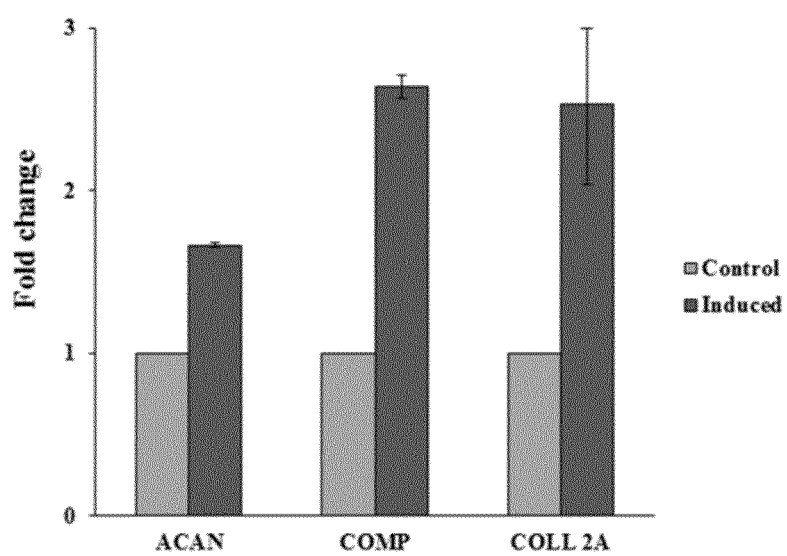
FIG. 14 shows the results of RT-PCR for the gene expression of collagen (Col) type II, aggrecan and cartilage oligomeric matrix protein (COMP) in the native MSCs (Control) and chondrogenic induced MSCs (Induced) according to the current invention. Values are given as the mean of three measurements±SEM.
Figure 15:
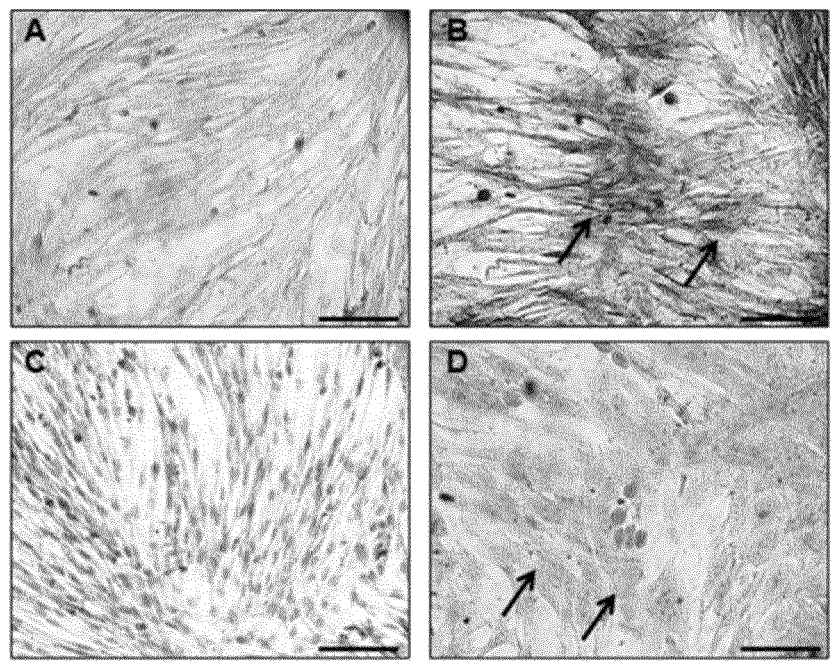
FIG. 15 shows representative images of peripheral blood (PB)-derived mesenchymal stem cells (MSCs) in their undifferentiated state (A & C) and chondrogenic induced (B & D) after Safranin O (A & B) and Alcian Blue (C & D) stainings. Glycosaminoglycan production (black arrows) can be noticed after induction. Scale bars represent 50 μm.
Figure 16:
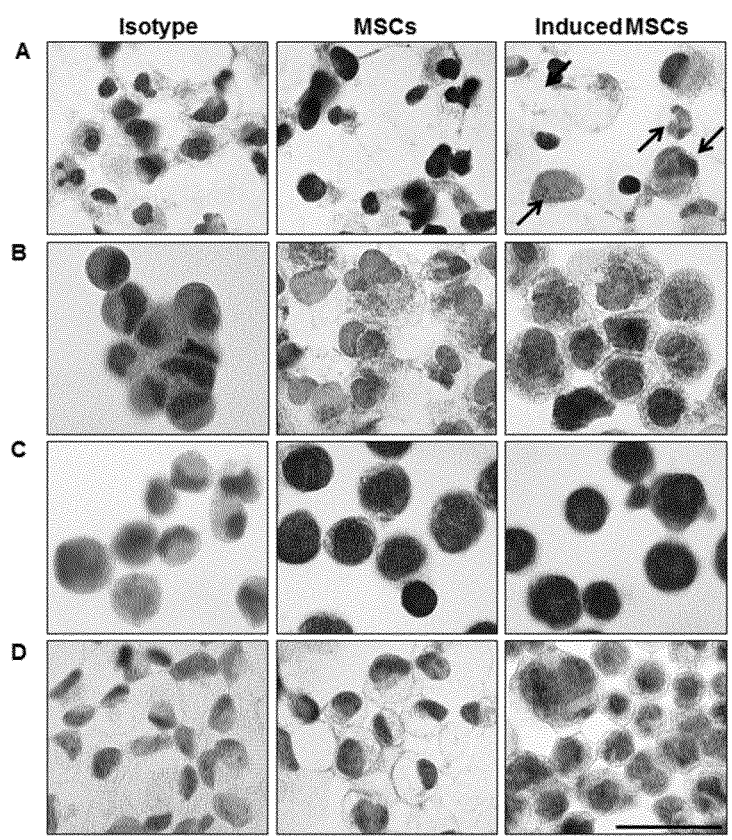
FIG. 16 shows results of immunocytochemistry on cytospins using Ki67 (A), collagen (Col) type II (B), vimentin (C) and p63 (D). Native mesenchymal stem cells (MSCs) were negative for p63 and positive for Ki67, Col II and vimentin, whereas chondrogenic induced MSCs were positive for p63, Col II and vimentin and slightly positive for Ki67. Arrows indicate a decreased signal for Ki67 in some chondrogenic induced MSCs. The relevant isotype controls were negative. Scale bar represents 25 μm.

Molecular markers suitable for screening and following the chondrogenesis include glycosaminoglycan production, collagen type II, p63, vimentin, major histocompatibility complex, aggrecan and/or cartilage oligomeric matrix protein (FIG. 16). Such expression may be analyzed by ways of (RT-)PCR (FIG. 14), flow cytomtry or immunochemistry. In addition, chondrogenesis may be followed by analyzing cell morphology (e.g. aided by use of HE, FIG. 13), or by stainings such as Alcian Blue staining or Safranin staining (FIG. 15).

Whereas native MSCs show a more stellate/spindled shaped morphology, MSCs induced into the chondrogenic lineage showed a more rectangular morphology.

Figure 4:
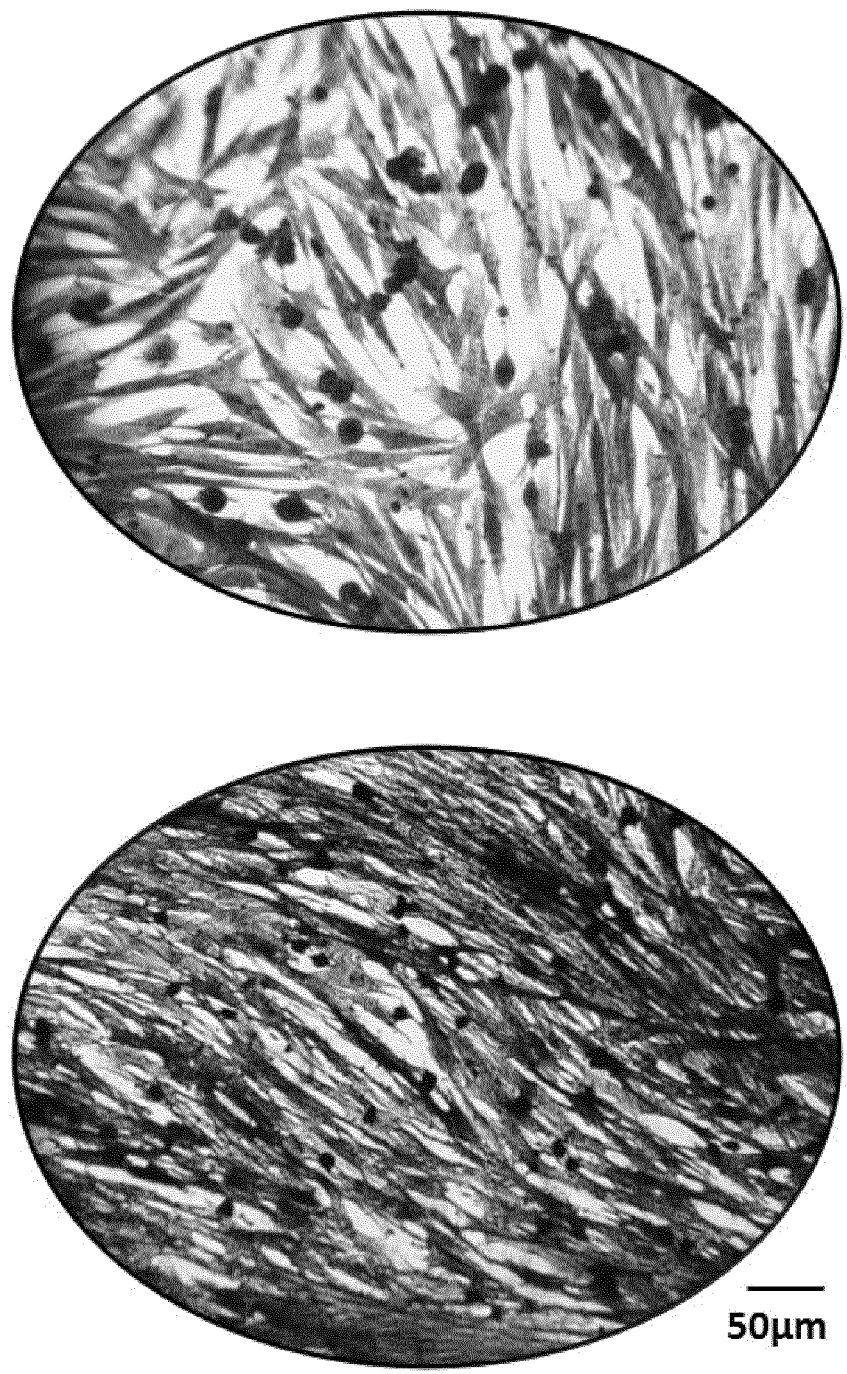
FIG. 4 shows immunohistochemistry data which revealed that the tenogenic induced mesenchymal stem cells (MSCs) according to an embodiment of the current invention were all positive for smooth muscle actin (SMA).
Figure 5:
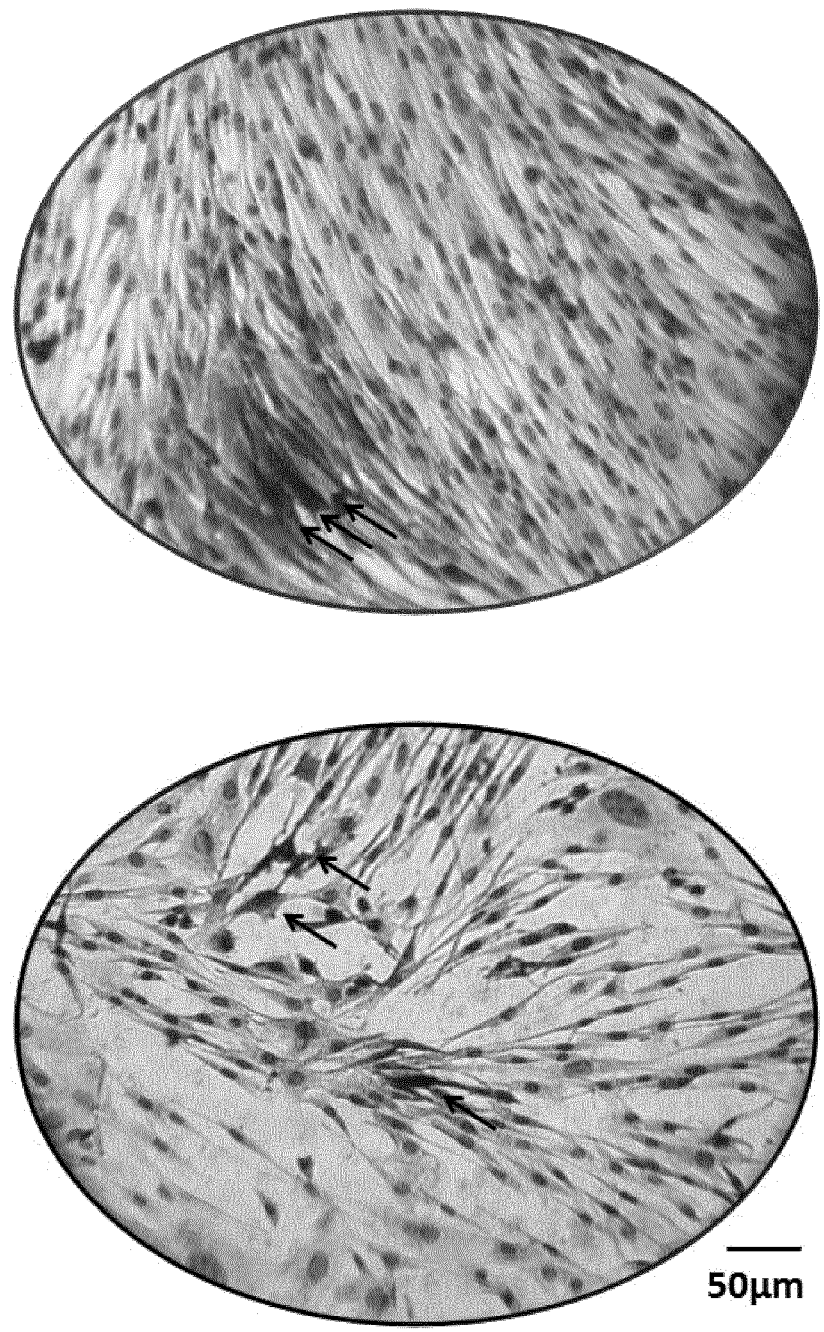
FIG. 5 shows immunohistochemistry data which revealed that some (arrows) of the tenogenic induced mesenchymal stem cells (MSCs) according to an embodiment of the current invention were positive for collagen type I. The typical tenogenic morphology and longitudinal orientation can be noticed on the images.

MSCs induced towards tenocytes are smooth muscle actin (FIG. 4) and collagen type I (FIG. 5). In addition, tenogenesis may be followed by analyzing cell morphology (e.g. aided by use of HE). Whereas native MSCs show a more stellate/spindled shaped morphology, MSCs induced into the tenogenic lineage showed a more stretched morphology and fiber orientation can be noticed.

The MSCs useful for the current invention may be derived by any standard protocol known in the art. Said MSCs may be derived from for instance bone marrow, (peripheral) blood, adipose tissue, neonatal birth-associated tissues including placenta (PL), umbilical cord (blood or tissue), amnion fluid, dermis, etc.

In one embodiment, the MSCs are isolated according to the method as described in BE2012/0656, PCT/EP2013/070247 or PCT/EP2013/070257 which entire content is incorporated here by reference.

More specifically, such method may comprises by preference the following steps:

a) the collection of one or more blood samples from donors, in a sample vial, coated with an anti-coagulant;

b) centrifuging the blood samples to obtain a 3-phase distribution, consisting of a plasma-phase, buffy coat, and erythrocytes phase;

c) collecting the buffy coat and loading it on a density gradient;

d) collecting of the blood-inter-phase obtained from the density gradient of step c);

e) isolating of mesenchymal stem cells from the blood-inter-phase by centrifugation;

f) seeding at least $2.5\times10^5$/cm$^2$ mesenchymal stem cells in culture and keeping them in a low glucose growth medium supplemented with dexamethasone, antibiotics and serum.

Preferably, in step f) minimally $2.5\times10^5$/cm$^2$ cells, even more preferred between $2.5\times10^5$/cm$^2$ and $5\times10^5$/cm$^2$ cells are seeded. This number is crucial to ultimately obtain a pure and viable population MSCs at an acceptable concentration. The density in which the cells in step f) are seeded, is essential, because planting the cells too dense will lead to massive cell death during expansion and a non-homogenous population of mesenchymal stem cells. A too low cell concentration, however, will result in little or no colony formation of mesenchymal stem cells, so that expansion is not or hardly possible, or it will take too much time. In both cases the viability of the cells will be negatively influenced.

By the term anti-coagulant, it is meant a composition that can inhibit the coagulation of the blood. Examples of anticoagulants used in the present invention include EDTA or heparin.

Figure 3:
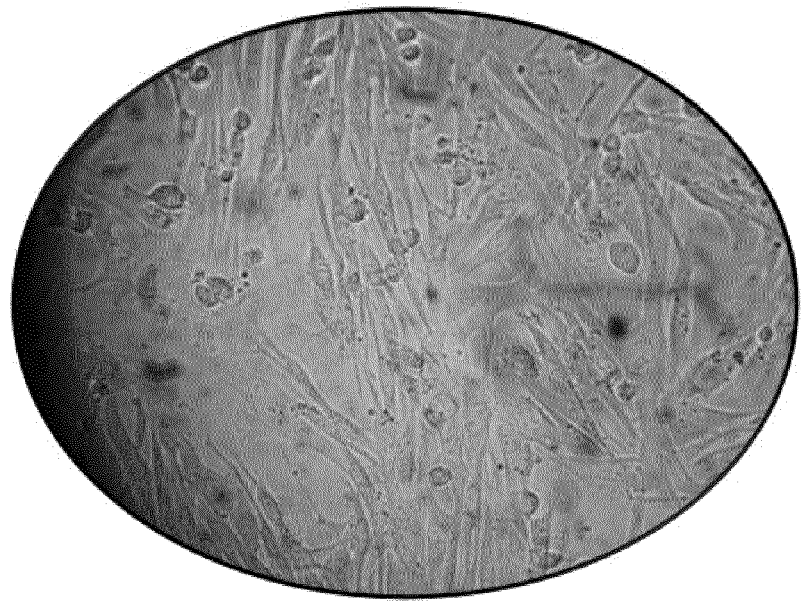
FIG. 3 shows representative light microscopic images of peripheral blood (PB)-derived mesenchymal stem cells (MSCs) in their undifferentiated state and after tenogenic induction. The typical tenogenic morphology and longitudinal orientation could be noticed after induction.
Figure 3:
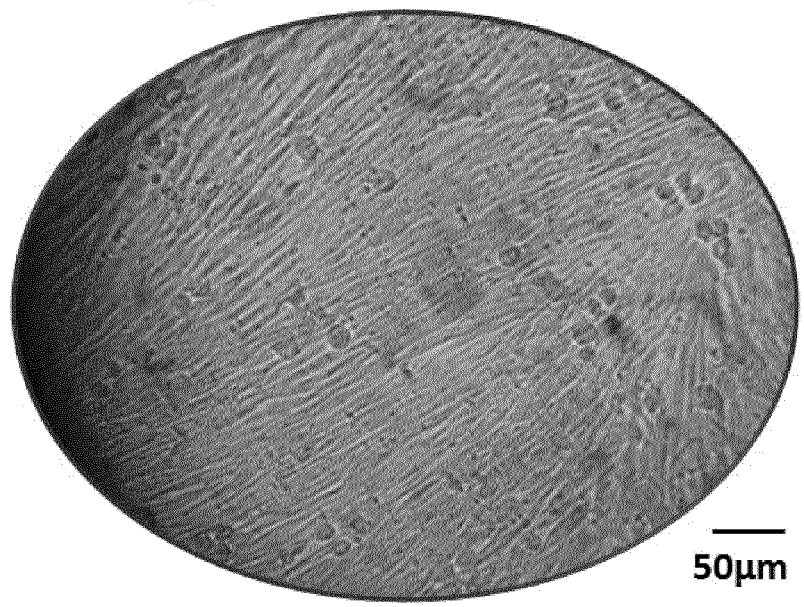

The term "buffy coat" in this invention, is to be understood as the fraction of non-coagulated blood, preferably obtained by means of a density gradient centrifugation, whereby the fraction is enriched with white blood cells and platelets. FIG. 3 shows a schematic representation of a 3-phase distribution of a blood sample obtained by means of centrifugation. The buffy coat is the middle phase B, located between the plasma-phase A and the erythrocyte-phase C.

In particular, the buffy coat will be isolated from the other fractions and diluted by means of a suitable physiological buffer, such as for example, a phosphate, bicarbonate, or Tris buffer, preferably with a minimum ratio of 1:2. This dilution factor is important, as lower dilution factors may lead to problems when loading the sample from step c on the density gradient, mainly due to a too heavy buffy coat fraction.

Preferably, the density gradient in step c and d of the present method is obtained by means of Percoll®. More in particular, the Percoll® will comprise a density between the de 1.08 g/ml and 1.077 g/ml.

The term blood-inter-phase is to be understood as that fraction of the blood, preferably obtained by means of a density gradient, located between the bottom fraction, mainly consisting of erythrocytes and polymorph nuclear cells, and the upper fraction, mainly consisting of plasma polymorph nuclear cells. The blood-interphase is the source of blood mononuclear cells (BMCs) comprising monocytes, lymphocytes, and mesenchymal stem cells.

By preference, the lymphocytes are washed away at 37° C., while the monocytes die within 2 weeks in the absence of cytokines necessary to keep them alive. In this way, the MSCs are purified. The isolation of the mesenchymal stem cells from the blood-inter-phase is preferably done by means of centrifugation of the blood-inter-phase (after isolation of the inter-phase), after which the cell pellet is washed at least once with a suitable buffer, such as a phosphate buffer.

In particular, the mesenchymal cells are kept at least 2 weeks in growth medium. Surprisingly, the dexamethasone in the growth medium will cause the stem cells to retain their specific characteristics and keep/prevent them from differentiating. Preferably, 1% dexamethasone is used.

Following a minimum period of 2 weeks (14 days), preferably 3 weeks (21 days) mesenchymal stem cell colonies will become visible in the culture bottles.

In a subsequent step g) at least $6\times10^3$ stem cells/cm$^2$ are transferred to an expansion medium containing low glucose, serum and antibiotics for the purpose of expanding the mesenchymal stem cells.

In particular, this medium will include a maximum of 20% serum (such as FBS or FCS). Too high serum concentrations can lead to a kind of "habituation phase" of the mesenchymal stem cells to the growth factors present in the serum, which can lead to a suboptimal division of the cells in the absence of serum. This can adversely affect the cells when they are used for regenerative purposes. Preferably, the expansion of the mesenchymal stem cells will occur in minimal five cell passages. In this way sufficient cells can be obtained. Preferably, the cells are split at 70 to 80% confluency. The mesenchymal stem cells can be maintained up to 50 passages in culture. After this the risk of loss in vitality, senescence or mutation formation occurs.

The cell population obtained by the method preferably consists of 90% mesenchymal stem cells. More preferably, it will consist of at least 95% mesenchymal stem cells, more preferably of at least 99%, most preferably 100%.

The nature of the cells obtained through this method can be ascertained by means of markers, specific for mesenchymal stem cells. Preferably, markers are selected from the group consisting of vimentin, fibronectin, Ki67, or any combination thereof. As such the purity of the obtained cell populations can be analyzed, and the percentage of mesenchymal stem cells determined.

Preferably, the stem cells used in the present invention are isolated from the blood of mammals, more preferably, from peripheral blood. By preference the used blood will originate from human, cat, dog or horse, most preferably equine derived.

In a possible embodiment, blood from a donor was used who was later also recipient of his isolated mesenchymal stem cells. In another embodiment, blood is used from donors in which the donor is preferably of the same family, gender or race as the recipient of the mesenchymal stem cells isolated from the blood of donors.

In particular, these donors will be tested on common current transmittable diseases or pathologies, in order to avoid the risk of horizontal transmission of these pathologies or diseases through the stem cells. Preferably, the donor animals are kept in quarantine. When using donor horses they can be, for example tested for the following pathologies: equine infectious anemia (EIA), equine rhinopneumonia (EHV-1, EHV-4), equine viral arteritis (EVA), West Nile virus (WNV), African Horse Sickness (AHS), Dourine (*Trypanosoma*), piroplasmosis, glanders (malleus, glanders), equine influenza A, Borreliosis (*Borrelia burgdorferi*, Lyme disease).

In a final aspect, the current invention also relates to a composition comprising MSCs induced towards tenocytes or chondrocytes; tenocytes or chondrocytes, obtained from a method as described above. Said composition preferably comprises between 1 and $10\times10^6$ cells/ml, preferably between 2 and $5\times10^6$ cells/ml. Said cells are by preference suspended in a suitable cell medium, such as for instance DMEM. In order to ensure the quality of the cells during cryopreservation, a suitable amount of cryoprotectant is added. Such cryoprotectant may for instance be DMSO. In a preferred embodiment, said DMSO is added in a volume of 10%. Cells are preferably kept at −80° C. prior to use.

Cells for freezing are obtained after an induction time of typically between 1 to 36 hours. Cultured cells are washed with a saline buffer such as PBS and treated with a solution comprising trypsin and/or EDTA for detaching the cells, preferably at a temperature of 37° C. After the cells have detached, trypsin action is inactivated by adding warm (37° C.) medium to the cells. The cell solution is subsequently centrifuged to obtain a cell pellet. Solution is preferably centrifuged at 300 G for a period between 5 and 10 minutes, more preferably 8 minutes, at room temperature. Supernatans is subsequently removed and cells are re-suspended towards the required cell concentration.

In particular, the composition is formulated for intravenous, intra-articular, intramuscular, intra-lesional administration to mammals. These modes of administration will depend heavily on the desired application of stem cells and/or their differentiated form.

In one embodiment, especially when said composition is used for joint or tendon pathologies, can be used with components selected from the group consisting of platelet-rich plasma (PRP), hyaluronic acid, compositions based on hyaluronic acid, glycosaminoglycans, or compositions based on glycosaminoglycans. Mixing of the composition with such carrier substances may in some cases be desirable to increase the effectiveness of the composition or create a synergistic effect. PRP, for example, a substance rich in growth factors, stimulate the stem cells after implantation. Preferably, both the stem cells and PRP are harvested from the same donors are for compatibility reasons. Carrier substances can also be used to counteract gravity: stem cells follow the law of gravity and therefore have difficulties reaching higher lesions without a carrier in which they can migrate. In addition, the carrier substances themselves also have beneficial effects on the pathological environment in which they contribute to the tissue repair itself and also provide a good stem cell niche to help differentiation of the cells in this area. Examples of hyaluronic acid, glycosaminoglycans or compositions on this basis include OSTENIL®, OSTENIL®+, Adant® and Adequan®.

The composition according to the present invention has very broad applicability. In particular, the composition is suitable for the following purposes:

treatment of trauma selected from the group comprising trauma of cartilage, tendon traumas, traumas of the ligaments, traumas of the bones, traumas of the mucus membranes, cysts or fractures treatment of neurological and neurodegenerative diseases selected from the group of Cushing's syndrome, respiratory paralysis or paresis of the extremities, and/or treatment of acute or chronic inflammatory disease states selected from the group of laminitis, periostitis, gastritis, osteoarthritis, inflammation—treatment of hypersensitivity reactions such as insect hypersensitivity (summer eczema for example), drug hypersensitivity, hypersensitivity to dust and other types of hypersensitivity.

In particular, comprises the current invention each application whereby a subject benefits from administering the composition to said subject. The subject may include a horse, cat, dog or human. More particularly, a method for administering a composition according to the present invention to a subject, may include the following steps:

a) thawing a sample bottle comprising the composition, frozen at at least −80° C., whereby thawing is carried out at a temperature between 20° C. and 37° C., preferably between 25° C. and 37° C., and in a time span of maximal 20 minutes, more preferably maximal 5 minutes;

b) aspirating the sample from the sample vial by means of a needle with an inner diameter of at least 0.3 mm, preferably at least 0.35 mm;

c) optional mixing of the composition with components selected from the group of platelet-rich plasma (PRP), hyaluronic acid or glycosaminoglycans;

d) administrating the composition or mixture thereof to a subject by intravenous, intra-articular, intramuscular, intralesional injection.

The cell diameter of the injection needle is crucial in this respect, in order to avoid damage to the cells. Defrosting the composition can be accomplished by thawing in a hot water bath or in the palm of one's hand or by any other method within the temperature limits.

Preferably, the composition is administered within 2 minutes after thawing, in order to safeguard the vitality of the composition.

In what follows, the invention is described on the basis of non-limiting examples which illustrate the invention, and are not intended to limit the scope of the invention.

EXAMPLES

Example 1: Cell Medium Composition

The following are examples of possible medium according to the current invention, useful for either tenogenesis or chondrogenesis. It is to be understood that the growth factors as defined in the tables below can be replaced by other growth factors of the same superfamily, or that the final concentration of a growth factor can be interchanged by a combination of growth factors of the same superfamily, whereby the sum of the concentrations of the combined growth factors equals the final concentration of the similar growth factor alone.

TABLE 1

| | Chondrogenic medium | | | | |
|---|---|---|---|---|---|
| | Medium A | Medium B | Medium C | Medium D | Medium E |
| FGF-2 | | | 3 ng/ml | 4 ng/ml | 5 ng/ml |
| TGF-β3 | 4 ng/ml | 3 ng/ml | 7 ng/ml | | 5 ng/ml |
| IGF-I | 120 ng/ml | | 210 ng/ml | 80 ng/ml | |

TABLE 2

| | Tenogenic medium | | | | |
|---|---|---|---|---|---|
| | Medium A | Medium B | Medium C | Medium D | Medium E |
| FGF-2 | 5 ng/ml | 7 ng/ml | 4 ng/ml | 10 ng/ml | 3 ng/ml |
| TGF-β3 | | 1 ng/ml | 3 ng/ml | | |
| IGF-I | | | | | 10 ng/ml |

Example 2: Marker Expression in Tenocyte and Chondrocyte Induced MSCs

Cells were seeded at a concentration of 6 to $14 \times 10^3$ MSCs/cm$^2$ in cell inducing medium. The following media were used:

Tenogenic medium: DMEM Low Glucose+20% FCS+1% P/S+5 ng/ml FGF-2

Figure 1B:
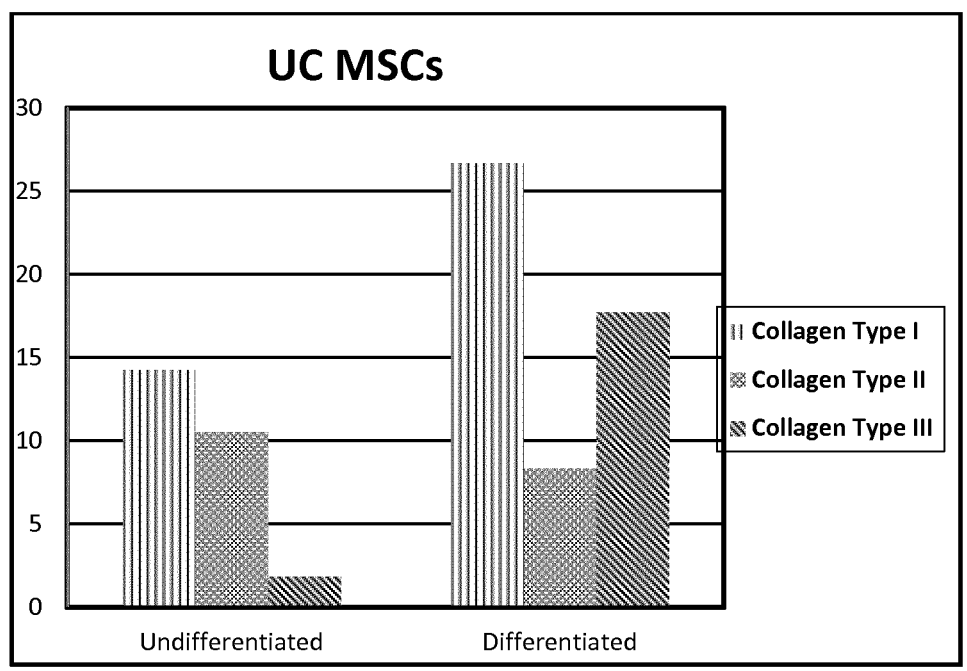

Chondrogenic medium: DMEM Low Glucose+20% FCS+1% P/S+4 ng/ml TGF-B3+120 ng/ml IGF-I In the chondrogenic induced cells, cartilage gene expression (Aggrecan (ACAN), Cartilage Oligomeric Matrix Protein (COMP) and Collagen 2A (COLL 2A)) were found to be increased after 1 day induction (see FIG. 1A) (RT-PCR results). In tenogenic induced cells, tendon gene increase (Collagen I and III) and cartilage gene decrease (Collagen II) was noticed within a time span of 1-7 days (depending on the experiment) (see FIG. 1B).

The results clearly demonstrate the variability in stem cell properties and pureness between the different sources.

Example 3: Tenogenic Potential from Human AT-MSCs, UC-MSCs or BM-MSCs

Figure 2A:
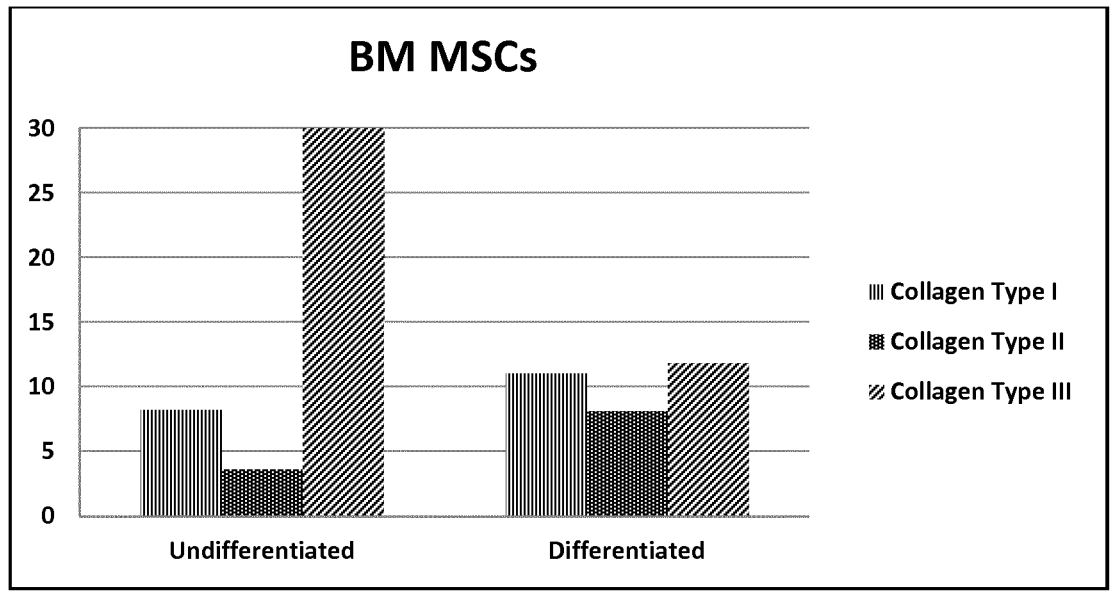
FIG. 2 shows the tenogenic potential of human MSCs derived from adipose tissue (AT), umbilical cord blood (UC) or bone-marrow derived MSCs (BM).
Figure 2B:
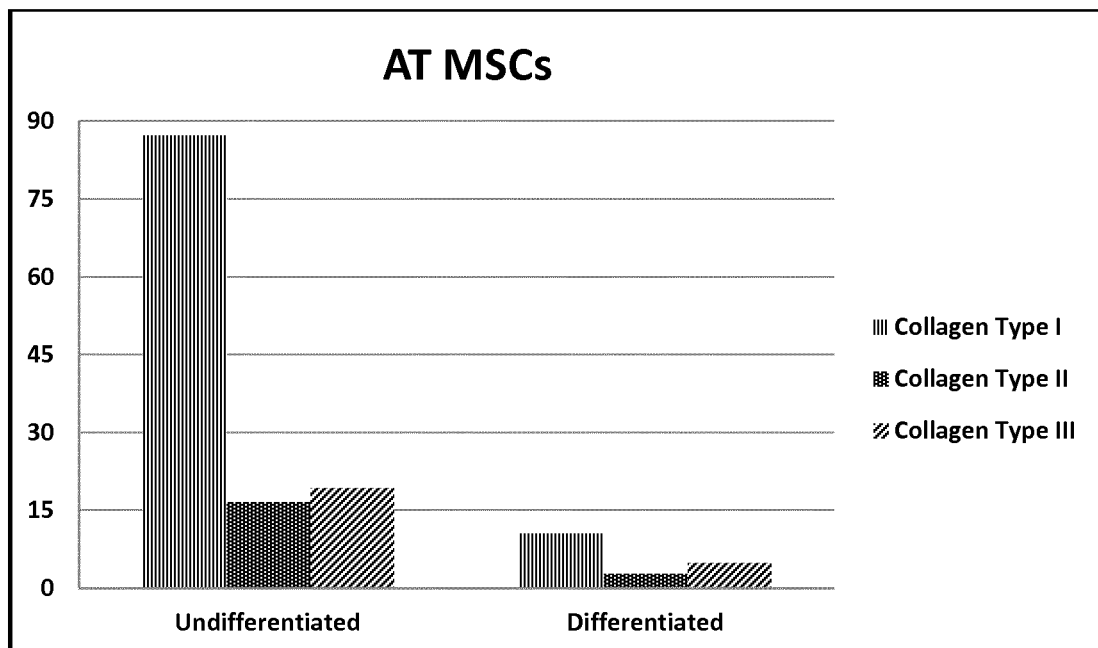
Figure 2C:
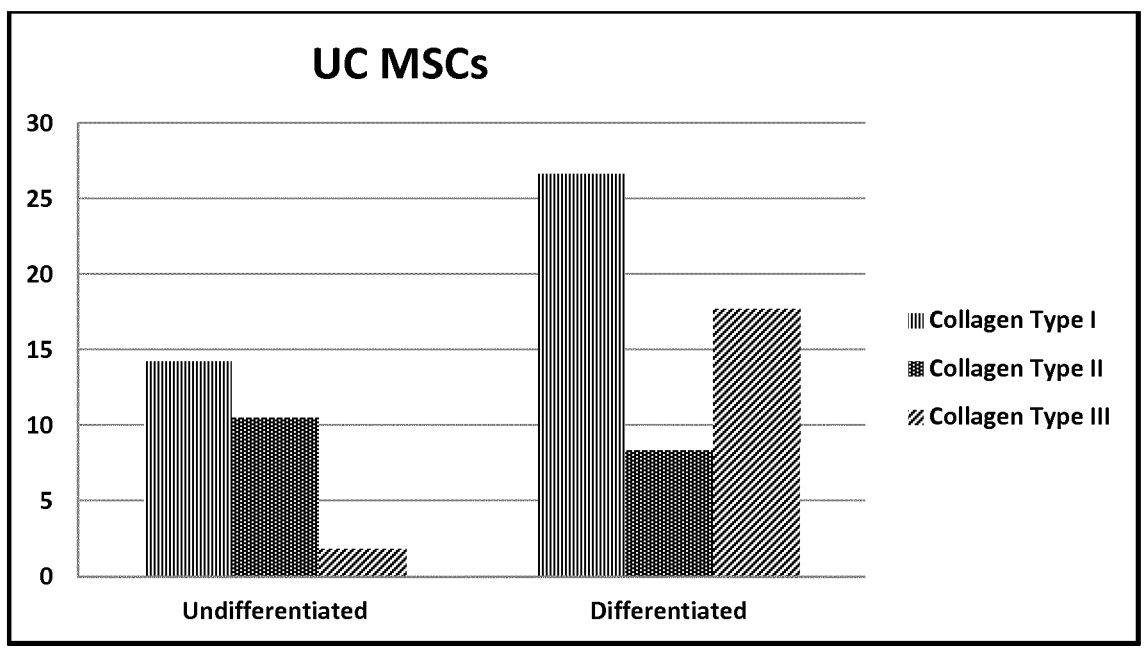

The inventors furthermore checked the difference in tenogenic "inducive" potential between MSCs derived from human adipose tissue (AT), umbilical cord blood (UC) or bone-marrow derived MSCs (BM). Cells were isolated according to known protocols. It was found that BM MSCs gave slightly better results than AT MSCs. The overall collagen ratio in AT-MSCs derived cells prior to induction is very high, which seems to have an impact on the induction and differentiation (resulting in a steep decrease in collagen type I and III) (FIG. 2A). The BM MSCs on the other hand, show a limited increase in collagen type I, yet a decrease in collagen type III, which is a good thing on the long run. However, an overall increase of both collagen types, preferably with a steeper collagen type I increase is to be pursued (to avoid a too long remodeling phase in vivo). The results of the UC MSCs embody this exactly (FIG. 2C): an increase in collagen type I and III, yet a higher level of collagen type I and a low amount of the cartilage collagen type II (as in the other groups).

In conservative tendon healing, the acute phase consists of an increase in collagen type III, which will be replaced by the more elastic collagen type I. With the tenogenic induced UC MSCs in humans or blood-derived MSCs, it is possible to mimic this increase in a faster rate, while avoiding a too long remodeling phase, because of the higher amount of collagen type I.

Example 4: Tenogenesis of Equine Peripheral Blood-Derived Mesenchymal Stem Cells a. Isolation and Tenogenic Induction of Mesenchymal Stem Cells (MSCs)

In total 50 ml of blood was collected in sterile EDTA tubes from the vena jugularis of the 6-years-old donor gelding for mesenchymal stem cell (MSC) isolation. At the same time, serum was collected and sent to Bose laboratory (Harsum, Germany) for testing on the following transmittable diseases: Equine infectious anemia (EIA), Equine rhinopneumonia (EHV-1, EHV-4), Equine Viral Arteritis (EVA), West-Nile Virus (WNV), Afrikan Horse Sickness (AHS), Dourine (*Trypanosoma*), Piroplasmosis, Malleus, Glanders, Equine Influenza A (equi I and II, American and European type) and Borreliosis (*Borrelia Burgdorferi*, the Lyme disease). Three weeks later, a second blood sample was sent to Bose again in order to confirm if antibody production was due to vaccination. After arriving in the lab, the 50 ml of blood was centrifuged at 1000G for 20 minutes and the buffy coat was collected and diluted 1:2 with phosphate-buffered saline (PBS). Afterwards, this suspension was gently layered on an equal amount of percoll (GE Healthcare). The further isolation was performed as described above. Then, 20 million peripheral blood mononuclear cells (PBMCs) were seeded per T75 flask in 3 flasks and cultured in culture medium. The medium was refreshed twice a week and the cells were maintained at 37° C. and 5% CO2. At 60% confluency the cells were trypsinized with 0.25% trypsin-EDTA and subcultured in tenogenic inducing medium (DMEM LG+20% FCS+1% P/S+FGF(-2) (5 ng/ml).) for 3 days. At the next confluency, the cells were trypsinized and resuspended in 1 ml of DMEM low glucose with 10% of dimethyl sulfoxide (DMSO, Sigma). At this point the cells were frozen overnight in isopropanol at −80° C. The samples were then stored in −80° C. and shipped on dry-ice before clinical application.

b. Preparation of Platelet-Rich Plasma (PRP)

In total 300 ml of peripheral blood was taken in a citrate phosphate dextrose adenine-1 (CPDA-1) single blood bag (Terumo®) for platelet-rich plasma (PRP) preparation. From this donor horse 25 samples of 1 ml PRP were prepared as previously described [Araki et al., 2012]. Each sample contained approximately $200 \times 10^6$ platelets and was frozen and stored at −80° C. before clinical application.

c. Immunohistochemistry

Immunohistochemistry (IHC) was performed to evaluate the expression of markers present on tenogenic induced MSCs. Cells were fixed for 10 minutes with 4% PF and permeabilized for 2 minutes with 0.1% Triton X at room temperature. Subsequently, cells were incubated with hydrogen peroxide (0.03%) for 5 minutes at room temperature and after washing with PBS, incubated for 2 hours at room temperature with the primary mouse IgG2a monoclonal anti-human smooth muscle actin (SMA) antibody (Dako, 1:200) and the rabbit IgG polyclonal anti-human collagen type IA2 (Col IA2) antibody (Abcam, 1:100). After washing with PBS, secondary ready to use goat anti-mouse and anti-rabbit peroxidase (PO)-linked antibodies (Dako) were added and incubated for 30 minutes at room temperature. Finally, 3,3'-diaminobenzidine (DAB) was added for 2-10 minutes and a counter staining with hematoxylin was performed to visualize the surrounding cells. As controls, identical stainings were performed on undifferentiated MSCs and background staining was assessed by using the proper isotype-specific IgG's. All isotypes were matched to the immunoglobulin subtype and used at the same protein concentration as the corresponding antibodies. Injecting mesenchymal stem cells (MSCs) and scoring system After thawing, the tenocytes (1 ml) and PRP (1 ml) were aspirated in the same syringe and intralesionally administered by means of ultrasound guidance. Twenty five acceptor horses were selected based on their injuries: a clear lesion had to be visible on the ultrasound at the lateral edge of the superficial digital flexor tendon (SDFT, n=10) or at the lateral branch of the suspensory ligament (SL, n=15). Clinical lameness was also noticeable in most of the cases. Afterwards, the horses were closely monitored for 1 week by means of a daily examination of their tendons and by observing possible adverse effects or hypersensitivity reactions (wheal formation, sweating, strong respirations or even fever). Subsequently, the tendons were evaluated at approximately 6 weeks post injection through ultrasound imaging and by lameness evaluation. Four veterinary practitioners were asked to give a score between 0 and 5 for their ultrasound images at approximately 6 weeks after the treatment. A score of 0 corresponded with 0% improvement or no ultrasonic improvement; 1=20% improvement or little ultrasonic improvement, but less than after conservative treatment; 2=40% improvement or greater ultrasonic improvement, as is usually seen after a successful conservative treatment; 3=60% improvement or better ultrasonic improvement than after successful conservative therapy; 4=80% improvement or very good ultrasonic improvement, much better than after successful conservative therapy, but not yet fully recovered; 5=100% improvement or no ultrasonic abnormalities, the tendon has the same consistency and fiber orientation as the contralateral tendon.

d. Isolation and Tenogenic Induction of Mesenchymal Stem Cells (MSCs)

After 17 days the first spindle shaped cells were noticed in the culture flasks and at 21 days after isolation the cells were trypsinized at approximately 60% confluency. Light microscopic images (LM) of the isolated cells as well as after tenogenic induction are depicted in FIG. 3. Undifferentiated MSCs had a stellate/spindle-shaped morphology and grew in colonies. After tenogenic induction, the cells showed a stretched morphology and fiber orientation could be noticed after 3 days of culturing in the tenogenic inducing medium.

e. Immunohistochemistry

After 3 days of tenogenic induction, the cells were all positive for smooth muscle actin (SMA) which strongly indicates that they gained in elasticity (FIG. 4). Moreover, some of the cells started to produce collagen type I, which is the functional tendon collagen (FIG. 5). These results implicate that tenogenic induction was successful, but that the cells were not terminally differentiated towards tenocytes, because the extracellular matrix production remained limited. This was in fact one of our objectives, since we were aiming to induce the MSCs towards tenocytes without producing all the extracellular matrix components in vitro before their in vivo application.

f. Scoring of the Ultrasound Images

Figure 6:
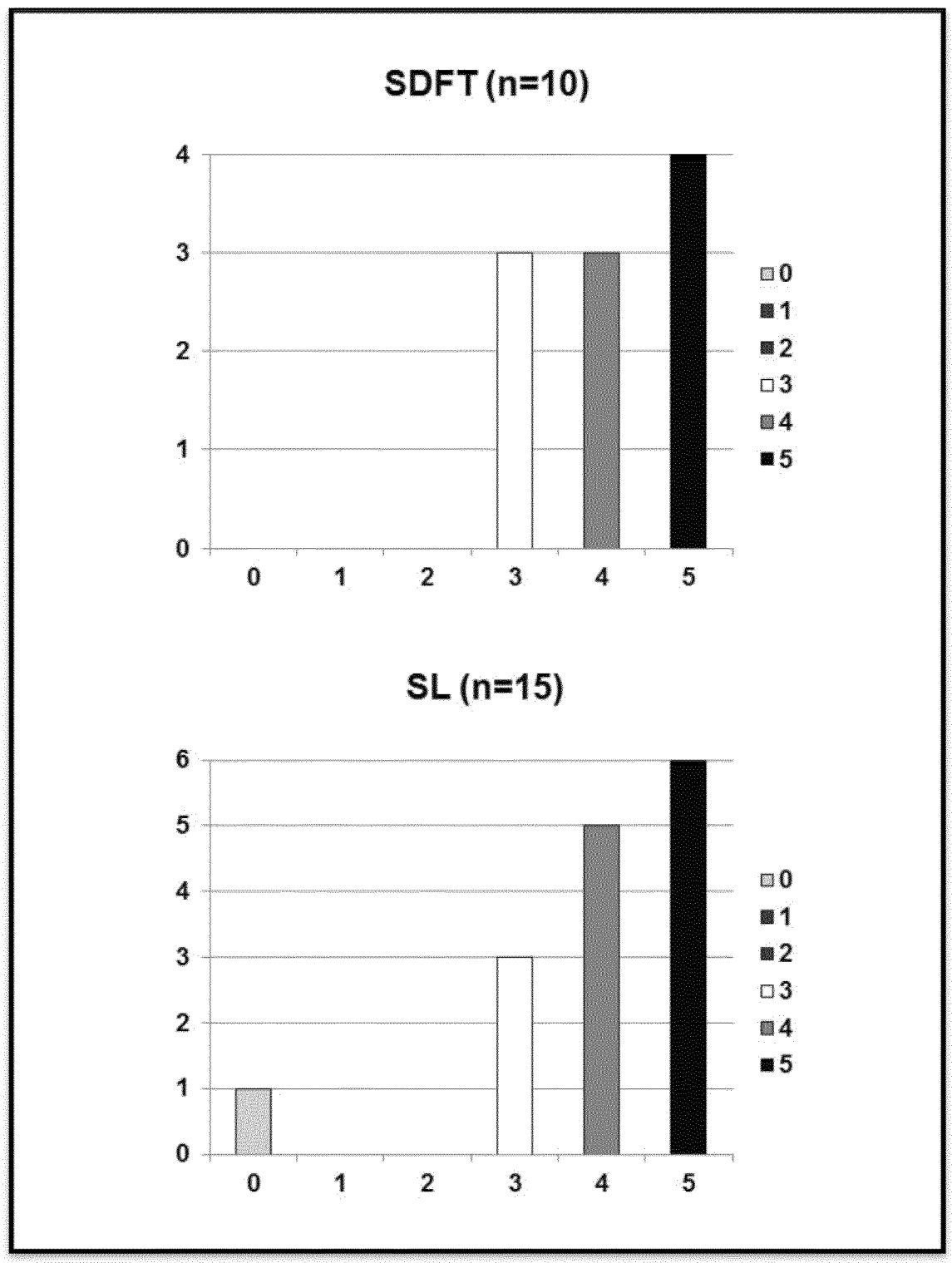
FIG. 6 shows histograms representing the number of patients and the different scores they received from the veterinary practitioners (0-5) at approximately 6 weeks after treatment of their superficial digital flexor tendon (SDFT) or suspensory ligament (SL). A score of 0 corresponded with 0% improvement or no ultrasonic improvement and 5 with 100% improvement or no ultrasonic abnormalities. Except for 1, all the patients (n=25) received at least a score 3 (60% improvement or better ultrasonic improvement than after successful conservative therapy).
Figure 7:
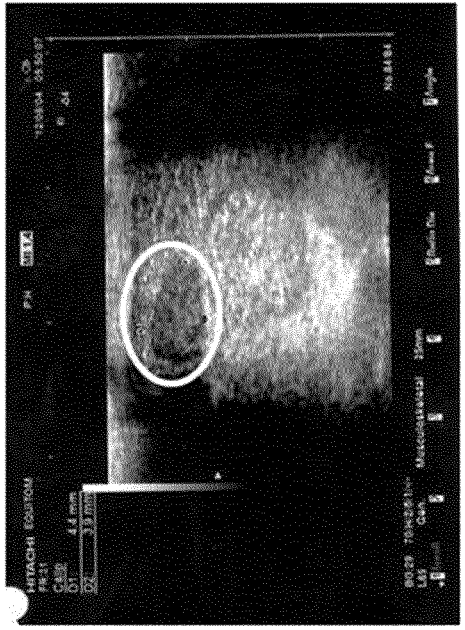
FIG. 7 shows a longitudinal (left side) and transversal (right side) ultrasound image of a lesion (white circle) in the lateral edge of the superficial digital flexor tendon (SDFT) of a horse. At 39 days after treatment with a tenogenic induced composition according to the current invention and PRP, a score 4 was given, because the fiber orientation was not completed yet on the longitudinal image (black circle).
Figure 7:
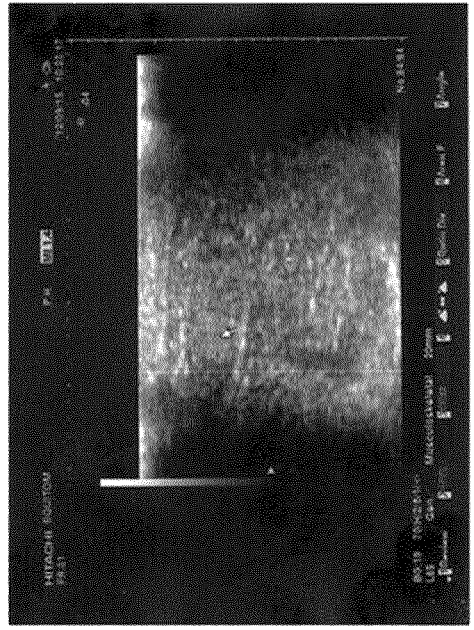
Figure 7:
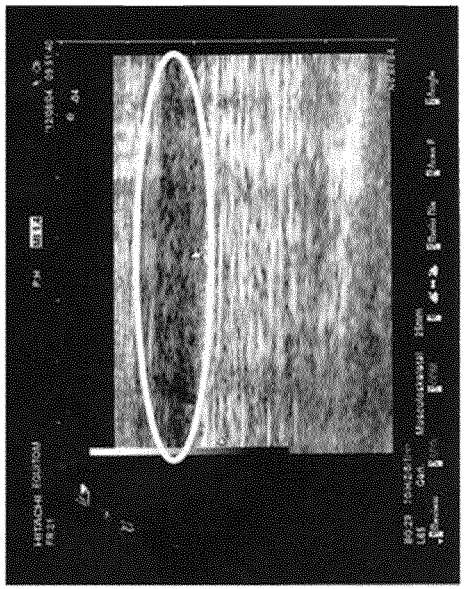
Figure 7:
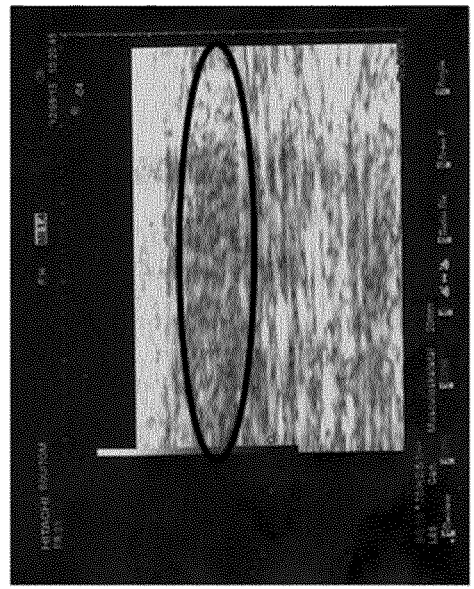
Figure 8:
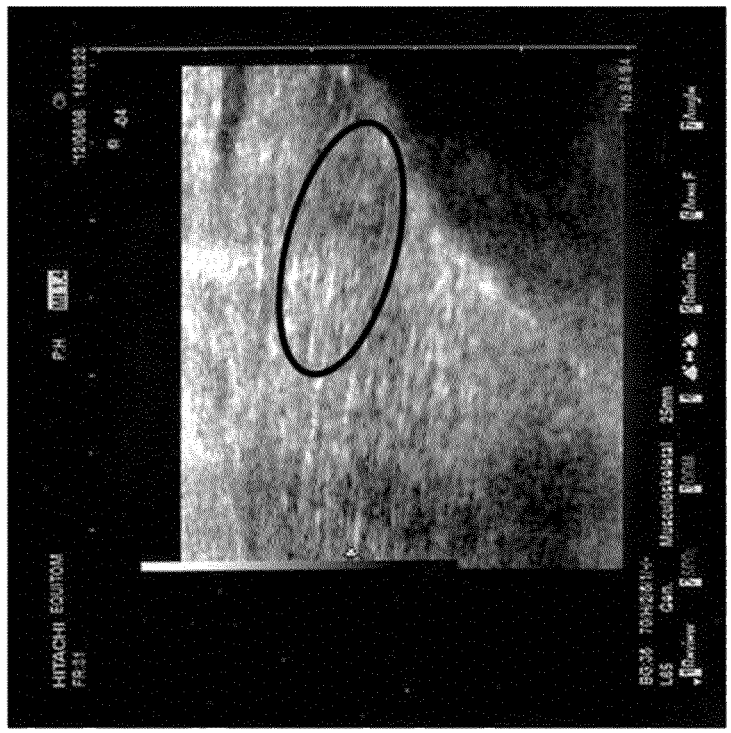
FIG. 8 shows an ultrasound image of a lesion (white circle) in the lateral branch of the suspensory ligament (SL) of a horse. At 35 days after the treatment with a tenogenic induced composition according to an embodiment of the current invention and PRP, a score 4 was given, because, although the fiber orientation was completed, there were still some small hypoechogenic zones (black circle). The black arrow indicates a zone of calcification.
Figure 8:
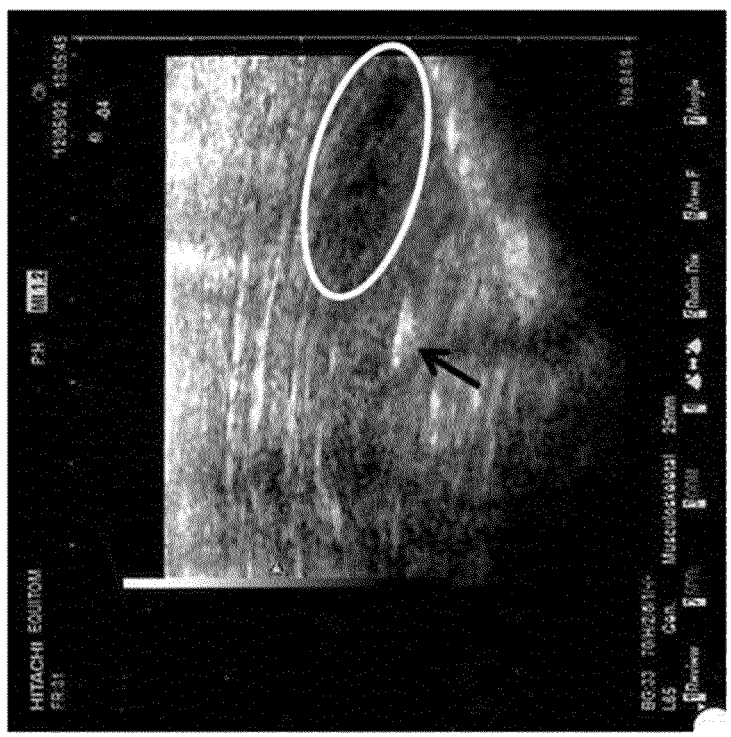

It has been reported that frozen equine PB-derived MSCs do not lose their stem cell characteristics [Martinello et al., 2010]. In this regard, the use of frozen tenogenic induced samples was defensible. After the treatment with allogenic tenogenic induced MSCs, the horses were closely monitored and no adverse effects could be noticed by the attending veterinarian nor by the owners. After approximately 6 weeks, in all 10 horses with a lesion in the lateral edge of the superficial digital flexor tendon (SDFT) a score 3 or more was given (60% improvement or better ultrasonic improvement than after successful conservative therapy) (FIG. 6). Indeed, the ultrasound images of FIG. 7 show that there is a substantial improvement 39 days after the treatment on the longitudinal (left images) as well as the transversal ultrasound images (right images). In addition, it should be mentioned that 4 out of the 10 horses (40%) even had a score 5 (100% improvement or no ultrasonic abnormalities, the tendon has the same consistency and fiber orientation as the contralateral tendon) at 6 weeks after the treatment (FIG. 6). After approximately 6 weeks, in 14 out of 15 horses with a lesion in the lateral branch of the suspensory ligament (SL) a score 3 or more was given as well (FIG. 6). Moreover, as for the SDFT lesions, 40% of the horses with a SL lesion (6 out of 15) received a score 5 (FIG. 6). Also here, ultrasound images revealed promising results as shown in FIG. 8. In addition, it should be noticed that even a calcification (black arrow) did not hinder the tenogenic induced MSCs to fill up the defect without further calcifying the tendon, which was the goal of the present study.

Figure 9:
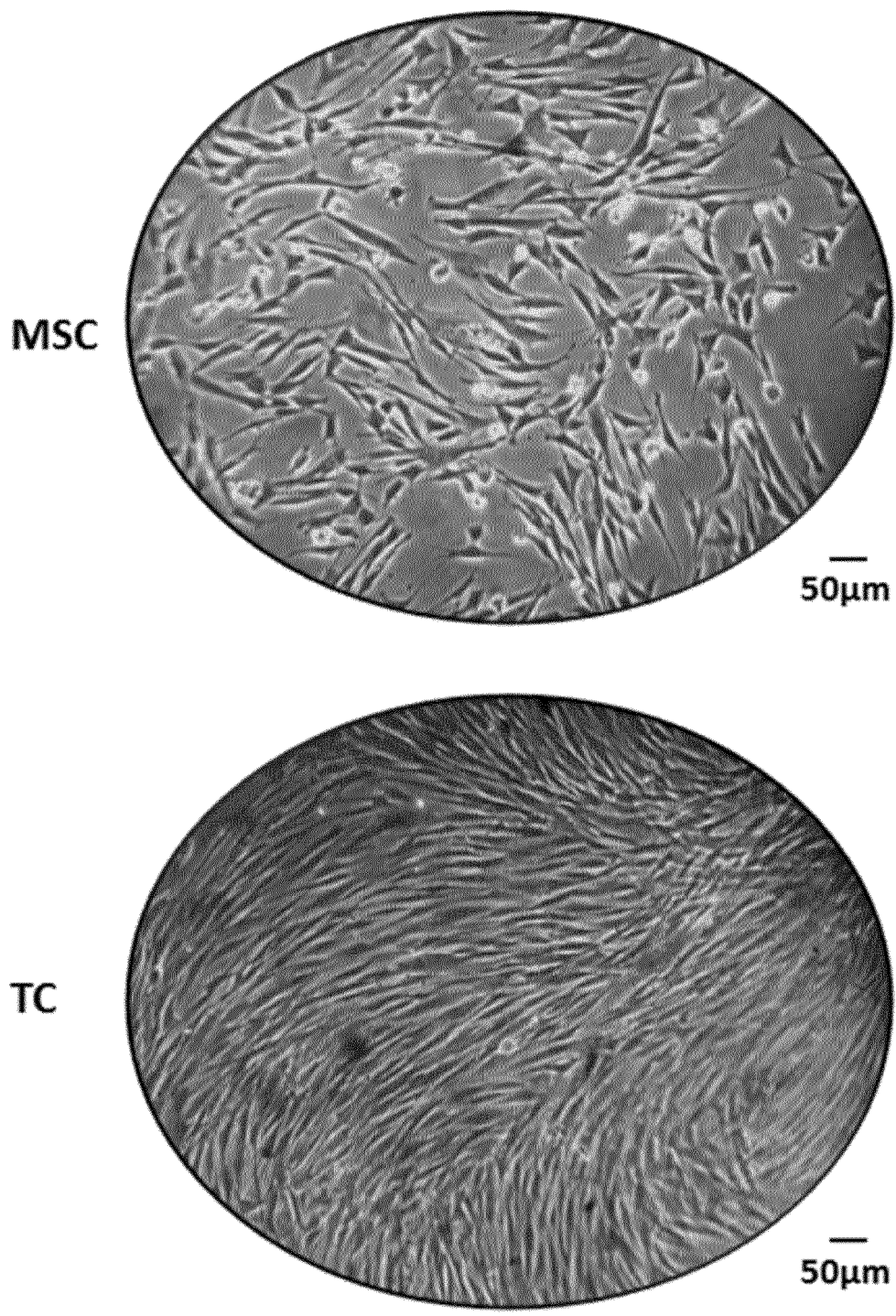
FIG. 9 shows representative light microscopic images at a 20× magnification of equine peripheral blood (PB)-derived mesenchymal stem cells (MSCs) in their undifferentiated state and after tenogenic induction according to an embodiment of the current invention. In contrast to the spindle shaped morphology of the MSCs, the typical lengthened tenogenic morphology and longitudinal orientation could be noticed in tenogenic induced cells.
Figure 10:
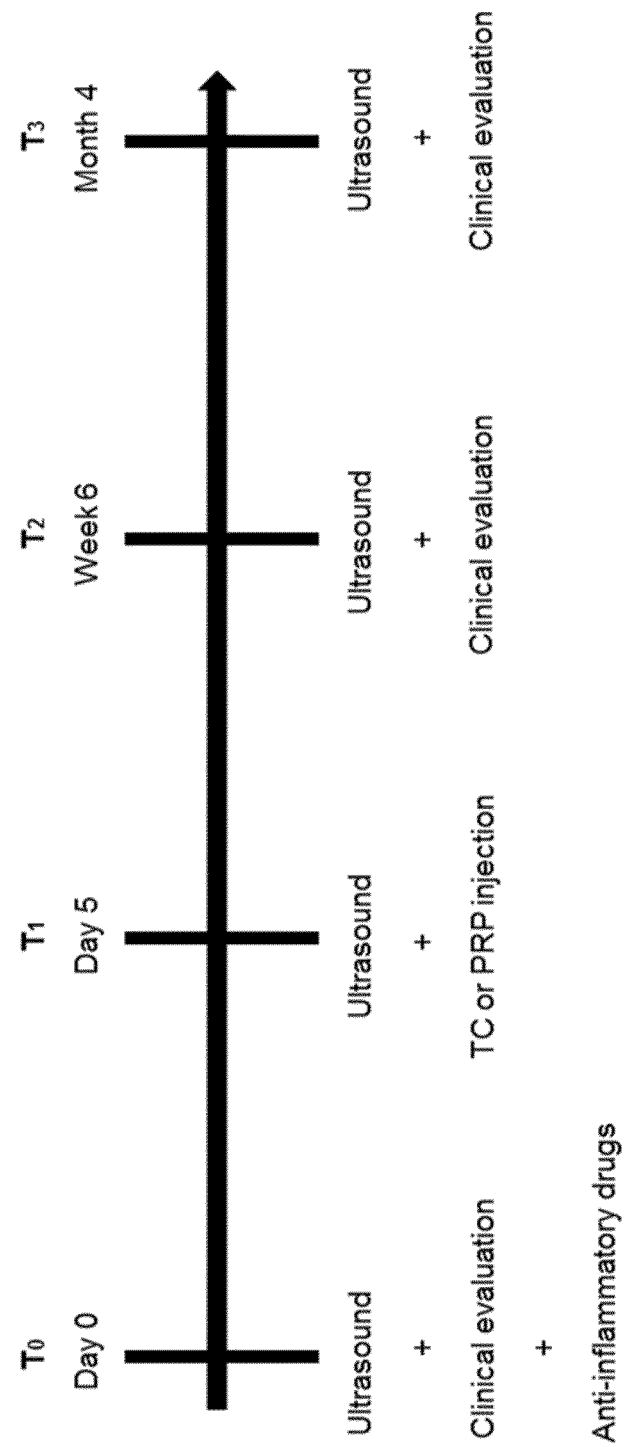
FIG. 10 represents a timeline of a treatment and follow-up protocol used in the present study at different time points (T).

Example 5: Desmitis of the Accessory Ligament of the Equine Deep Digital Flexor Tendon: A Regenerative Approach MSCs and PRP were prepared as described in Example 4.
a. Case Selection and History
Eight adult Warmblood show jumping horses were included in this study. The horses showed the following clinical signs: acute lameness in one of the front limbs (one of the horses was lame after a jumping exercise), swelling, warmth and sensitivity in the area of the accessory ligament of the deep digital flexor tendon (ALDDFT). Moreover, all lesions of the ALDDFT had to be clearly detectable on ultrasound examination, and none of the horses could have received any treatment before inspection by the non-blinded attending veterinarians. In addition, horses with lesions in other structures besides the ALDDFT were excluded from the study.
b. Treatment Protocol
When desmitis of the ALDDFT was diagnosed, the horses were initially treated conservatively for 5 days with non-steroidal anti-inflammatory drugs (NSAIDs), resting, cooling and a compressive bandage in order to reduce the swelling of the region and obtain optimal conditions for the intralesional injection. After conservative treatment, an intralesional injection of PRP or a tenocyte induced cell composition according to the current invention was randomly assigned to each horse and performed using ultrasound guidance. All 8 horses were immobilized (box rest) for 3 weeks, followed by daily walking exercises for 5 to 10 minutes for another 3 weeks. The first follow-up was planned 6 weeks after the injection. A second clinical and ultrasonographic examination was performed at 4 months after treatment.
c. Evaluation Protocol
The horses were re-evaluated clinically and ultrasonographically 6 weeks and 4 months after the injection with PRP or the cell composition. The clinical examination consisted of a visual inspection, palpation for the presence of swelling and/or heat, general inspection of the patient and a concise lameness evaluation. A thorough ultrasound examination was performed at the lesion site. There were several reasons for performing ultrasonographic diagnoses. The ease, safety and non-invasiveness of this method permitted not only a morphologic in vivo evaluation of the lesions, but, more importantly an observation over time. Thanks to the technological advances and decreasing equipment cost, this imaging modality is very useful and readily available in practice. Two veterinary practitioners were asked to give a score between 0 and 5 for the ultrasound images of all the patients. The scoring system was adapted from a previous study about superficial digital flexor tendinitis and desmitis of the suspensory ligament by Broeckx et al, 2012. The threshold for improvement after successful conservative therapy was set at maximal 40% at 6 weeks and 60% at 4 months after conservative treatment. A score of 0 corresponded with 0% improvement or no ultrasonographic improvement; 1=20% improvement or little ultrasonographic improvement; 2=40% improvement or the same ultrasonographic improvement as expected after 6 weeks of conservative treatment; 3=60% improvement or better ultrasonographic improvement as expected after 6 weeks of conservative treatment or the same ultrasonographic improvement as expected after 4 months of conservative treatment; 4=80% improvement or very good ultrasonographic improvement, much better than seen after 4 months of conservative treatment, but not yet fully recovered; 5=90-100% improvement or (nearly) no ultrasonographic abnormalities, the ligament has (almost) no hypo-echoic foci and (nearly) the same fiber orientation as the contralateral ligament.
c. Isolation and Tenogenic Induction of Mesenchymal Stem Cells (MSCs)
Blood was sampled according to an ethically approved methodology. After 17 days the first spindle shaped cells were noticed in the culture flasks and at 21 days after isolation the cells were trypsinized at approximately 60% confluency. The isolated cells had a stellate/spindle shaped morphology (FIG. 9) and fulfilled all the requirements to be typed as mesenchymal stem cells (MSCs). After 3 days of tenogenic induction, the cells showed a stretched morphology and fiber orientation in vitro (FIG. 9). The samples were stored in a −80° C. ultralow temperature freezer (Haier, Elscolab) and shipped on dry-ice before clinical application. After thawing, an average cell viability of 85% was noticed in all the samples.
d. Preparation of Platelet-Rich Plasma (PRP)
Concerning the platelet-rich plasma (PRP) preparation, each sample contained approximately $200 \times 10^6$ platelets per ml and was frozen and stored at 1 ml per sample in a −80° C. ultralow temperature freezer (Haier, Elscolab) before clinical application. In addition, it has to be mentioned that for all the tenocyte induced compositions and PRP samples bacteriological, fungal and yeast examinations were performed. Obviously, only the samples that were negative for the microbiological examinations were released for clinical use. To ensure conformity in the study, a liquid form of PRP was used. In this regard, we were able to compare the tenocyte induced composition with PRP using the same treatment protocol and similar carrier fluids.
e. Patient Follow-Up
In the days following the intralesional injection, particular attention was paid to observing any possible adverse effect or hypersensitivity reaction, which would be noticeable in the form of wheal formation (physical reaction), local warmth, sweating, heavy breathing or fever. In all 8 horses there were no signs of any of the general adverse effects, which could have been expected, since the horses were injected locally. In contrast with the tenocyte induced composition treated patients, the 4 horses treated with PRP showed a more pronounced swelling during 5 days after injection, which disappeared without medical treatment (FIG. 10). At the re-evaluations at 6 weeks and 4 months post injection (FIG. 10), none of the horses presented local adverse effects after treatment with PRP or the tenocyte induced composition in the accessory ligament of the deep digital flexor tendon (ALDDFT).

Figure 11:
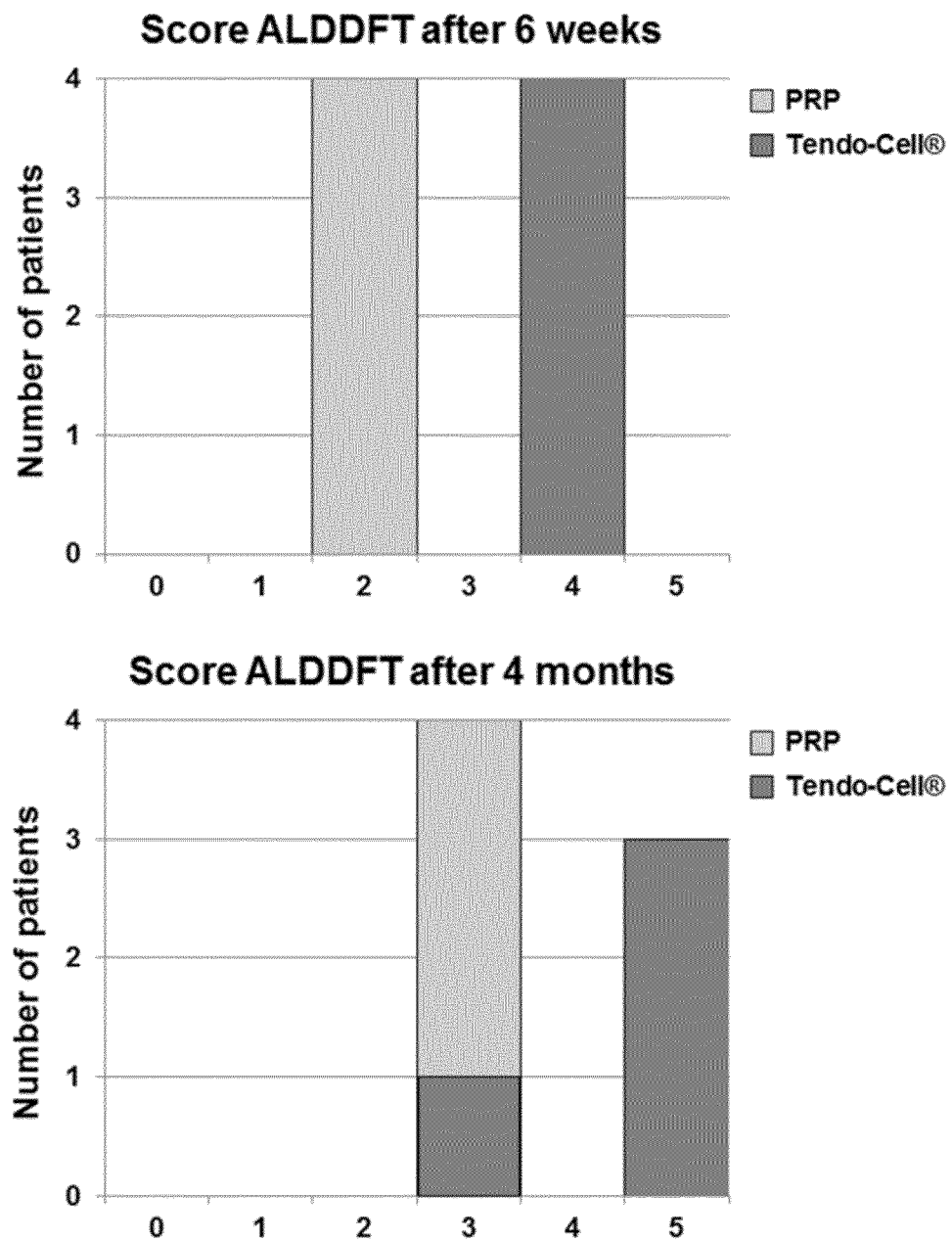
FIG. 11 shows histograms which represent the number of patients and the different scores they received from the veterinary practitioners (0-5) at approximately 6 weeks and 4 months after treatment of their accessory ligament of the deep digital flexor tendon (ALDDFT). At 6 weeks after treatment with platelet-rich plasma (PRP), all 4 patients (light grey) received a score 2/5. At the same time point, all 4 a tenogenic induced treated patients (dark grey) received a score 4/5. At 4 months after PRP treatment, all the patients received a score 3/5. Although 1 of the tenogenic induced treated patients received the same score, the other 3 patients received a score 5/5.
Figure 12:
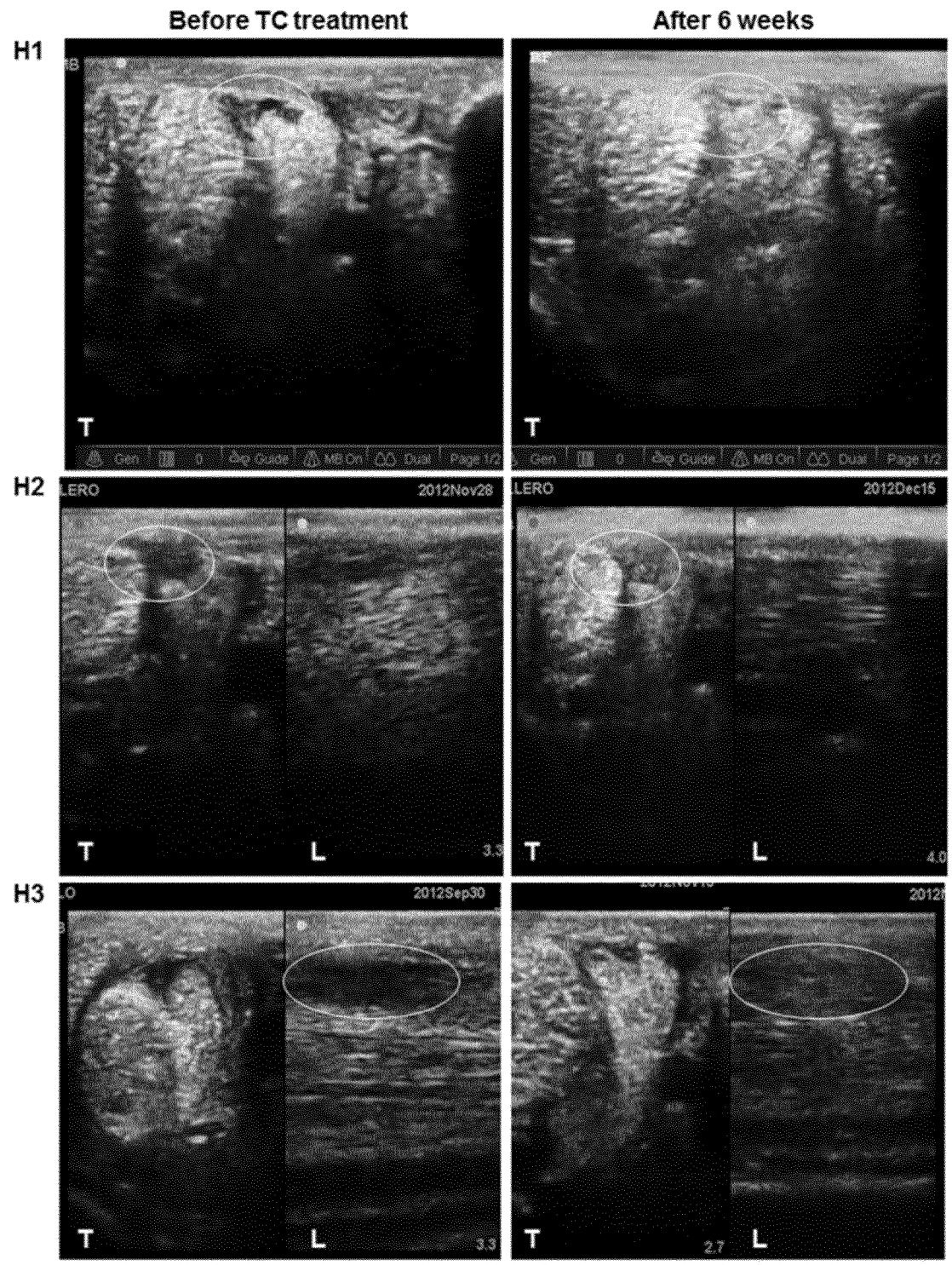
FIG. 12 shows transversal (T) and longitudinal (L) ultrasound images of a lesion (white circle) in accessory ligament of the deep digital flexor tendon (ALDDFT) in 3 horses (H) before (left column) and 6 weeks after (right column) treatment with tenogenic induced allogenic mesenchymal stem cells (TC). At approximately 6 weeks after the treatment, a score 4 was given to all the treated ALDDFTs, because, although the fiber orientation was completed, there were still some small hypo-echoic zones.

All the horses treated with PRP were still lame at approximately 6 weeks post injection, the ALDDFT region was faintly swollen and ultrasound images were only slightly improved. Therefore, a score 2/5 was given by 2 independent veterinarians to all 4 patients (FIG. 11). In the tenocyte induced treated group, on the other hand, all 4 horses were clinically sound, the swelling disappeared and the same 2 independent veterinarians gave a score 4/5 for the ultrasound images at 6 weeks after intralesional injection (FIG. 11). This implicates that the lesions improved about 80% on the ultrasound images, which was much better than the 40% improvement in the PRP treated group. FIG. 12 represents the ultrasound images of 3 patients before and 6 weeks after treatment with tenocyte induced cell composition. A considerable filling of the lesions could be noticed in all cases. Still, the lesions were not completely filled, and therefore, the patients were advised to continue and increase the walking exercise for 3 more weeks, followed by trotting exercise until 4 months after the treatment.

Four months after the intralesional PRP injections, the horses were faintly lame (only visible under certain circumstances) and the attending veterinarians assigned a score 3/5 (FIG. 11), which was still not comparable with 6 weeks after tenocyte treatment. At 4 months after tenocyte treatment, 3 of the 4 horses received a score 5/5 and went back to full training. However, 1 of the 4 horses slightly relapsed (non-pronounced lameness) and received a score 3/5, as in the PRP group (Table 4, FIG. 11). In conclusion, this study reports a positive clinical and ultrasonographical outcome after tenogenic induced MSC treatment of desmitis of the equine ALDDFT, whereas no considerable improvements could be noticed after treatment with allogenic PRP.

Example 6: Regenerative Therapies for Equine Degenerative Joint Disease

MSCs and PRP were prepared as described in Example 4.

a. Chondrogenic Induction of Mesenchymal Stem Cells (MSCs)

After MSC isolation, cells were seeded at $6.7 \times 10^3$ MSCs/cm$^2$ in T75 flasks for chondrogenic induction. Chondrogenic induction medium comprisee of DMEM Low Glucose, 20% FCS, 1% AB/AM and 4 ng/ml TGF-β3+120 ng/ml IGF-I. At 60% confluency, chondrogenic induced cells were trypsinized, resuspended in 1 ml of DMEM low glucose with 10% of dimethyl sulfoxide (DMSO, Sigma) and frozen before being shipped on dry-ice for clinical application.

b. Preparation of Platelet-Rich Plasma (PRP)

In total, 300 ml of peripheral blood was taken in a citrate phosphate dextrose adenine-1 (CPDA-1) single blood bag (Terumo®) for platelet-rich plasma (PRP) preparation. From this donor horse, 30 samples of 1 ml PRP were prepared. Each sample contained approximately 200×106 platelets and was frozen and stored at −80° C. before clinical application.

c. Cytological Staining

Hematoxylin (HE), Crystal Violet (CV), Alcian Blue (AB) and Safranin O (SO) staining (all from Sigma) were performed on MSCs and chondrogenic-induced MSCs, as indicated by the manufacturer. Both HE and CV staining were carried out in order to visualize the cell morphology and cellular organization. Furthermore, AB and SO staining were performed to give an indication of the presence of acid polysaccharides, such as glycosaminoglycans in cartilage-like structures.

d. Immunocytochemistry

Immunocytochemistry was performed to evaluate the expression of collagen type II (Col II), Ki67 (proliferation marker), p63 (tumor suppression gene) and vimentin (mesenchymal cell marker) on native MSCs and chondrogenic-induced MSCs after trypsinization and cytospin preparation at 700 rpm for 4 minutes. Cells were fixed for 10 minutes with 4% PF and permeabilized for 2 minutes with 0.1% Triton X at room temperature. Subsequently, cells were incubated with hydrogen peroxide (0.03%) for 5 minutes at room temperature and after washing with PBS, incubated for 30 minutes at room temperature with the primary rabbit IgG polyclonal antibodies recognizing: Col IIA1 (1:50), Ki67 (1:200) and p63 (1:100) and mouse IgG1 monoclonal anti-vimentin (1:100) (all from Abcam). After washing with PBS, secondary ready-to-use goat anti-mouse and anti-rabbit peroxidase (PO)-linked antibodies (Dako) were added and incubated for 30 minutes at room temperature. Finally, 3,3'-diaminobenzidine (DAB) was added for 5 minutes and a counter staining with hematoxylin was performed to visualize the surrounding cells. As controls, identical staining was performed on undifferentiated MSCs and background staining was assessed by using the proper isotype-specific mouse monoclonal or rabbit polyclonal antibody. All isotypes were matched to the immunoglobulin subtype and used at the same protein concentration as the corresponding antibodies. Wherever appropriate, equine tendon or skin tissue sections were used as negative controls.

e. Flow Cytometry

To characterize the MSCs immunophenotypically, the expression of several stem cell markers was evaluated by flow cytometry. The expression of the typical rejection proteins, major histocompatibility complex (MHC) class I and II was evaluated on native and chondrogenic induced MSCs. Per series, 400,000 cells were used and labeled with the following primary antibodies: mouse anti-horse MHC class I IgG2a (Washington State University, 1:50) and mouse anti-horse MHC class II IgG1 (Abd Serotec, 1:50). Cells were incubated with the primary antibodies for 15 minutes on ice in the dark and washed twice in washing buffer, consisting of DMEM with 1% bovine serum albumin (BSA). A secondary rabbit anti-mouse-FITC (Abcam, 1:100) antibody was used to identify positive cells after 15 minutes of incubation on ice in the dark. Finally, all cells were washed three times in washing buffer and at least 10,000 cells were evaluated using a fluorescence activated cell sorter (FACS) Canto flow cytometer (Becton Dickinson Immunocytometry systems) equipped with a 488 nm solid state and a 633 nm HeNe laser, and these data were subsequently analysed with the FACS Diva software. All analyses were based on (i) autofluorescence and (ii) control cells incubated with isotype-specific IgG's, in order to establish the background signal. All isotypes were matched to the immunoglobulin subtype and used at the same protein concentration as the corresponding antibodies.

f. Gene Expression Analysis by Real-Time RT-PCR

Equine MSCs in passage 3 were seeded in T25 flasks at a density of 8,000 MSCs/cm2 with either expansion medium (minus the chondrogenic inducing factors) or chondrogenic induction medium for 30 hours. After treatment, cells were lysed in 2 ml of Trizol (Invitrogen) and the lysate was separated into aqueous and organic phases by chloroform separation (300 µl, Sigma-Aldrich). The aqueous phase was recovered after centrifugation and total RNA was precipitated by using equal volumes of isopropanol. The precipitate was washed with 75% EtOH once and then solubilized with 25 µl of RNAse free water and quantified on the Nanodrop Lite (Fisher Scientific) before reverse transcribing 1 µg of RNA, using the TaqMan Reverse Transcription Reagents Kit (Life Technologies). Gene expression analysis was performed in triplicate (30 ng of cDNA in each reaction) with TaqMan Gene Expression Assays (Life Technologies) (Table 3) on the CFX96 Real-Time PCR System (Biorad). Values were normalized to GAPDH mRNA as internal control and presented as fold change, compared to native MSCs (i.e. in expansion medium), using the comparative CT method (=2-ΔΔCT method).

TABLE 3

TaqMan gene expression assays used for real-time RT-PCR

| Target gene | Assay ID |
| --- | --- |
| Aggrecan | Ec03469667_m1 |
| Collagen II | Ec03467386_g1 |
| COMP | Ec03468079_g1 |
| GAPDH | Ec03210916_gH | g. Patient Inclusion Criteria

For a first study, 20 acceptor horses were selected based on their injuries. Clinical lameness had to be present in a mild to moderate form for at least 3 months and had to be attributable to fetlock joint osteoarthritis. In this regard, the location of the lameness had to be confirmed by a positive intra-articular anesthesia of the fetlock joint, a mild to moderate positive flexion test and a certain degree of joint effusion. Furthermore, signs of osteoarthritis such as osteophytes and/or cartilage defects had to be noticeable on CT and/or radiography. For a second study (comparing 2 combination treatments), 30 horses were selected using the same inclusion criteria. Untreated or placebo animals could not be included in the present study, since only owner horses with naturally occurring DJD were used.

Injecting Mesenchymal Stem Cells (MSCs) and Monitoring of Adverse Reactions

In the first study, horses were randomly assigned to PRP, native MSCs, native MSCs plus PRP (Combination 1), or chondrogenic-induced MSCs plus PRP (Combination 2) treatment. In the second study, horses were randomly assigned to one of the two combination therapies. After thawing, both MSCs and PRP were aspirated in the same syringe (for combination groups) and administered intra-articulary. After the treatment, the horses were closely monitored for 1 week by means of a daily examination of the injected joint and by observing the occurrence of possible adverse effects or hypersensitivity reactions (wheal formation, sweating, strong respirations or even fever). Subsequently, the joints were evaluated at approximately 6 weeks (T1), 12 weeks (T2), 6 months (T3) and 12 months (T4) post injection through clinical evaluation by 2 independent veterinarians for all horses. In the second study, horses were randomly assigned to one of the two combination therapies and evaluated at T1. The experimental design was approved by an ethical committee.

h. Clinical Scoring System

In order to evaluate the severity of the clinical condition, the following parameters were graded by the same veterinarians at the aforementioned time points (T0-4): clinical lameness from 0 to 5 (0=no lameness and 5=minimal weight bearing lameness) according to the American Association of Equine Practitioners (AAEP), response to flexion test from 0 to 3 (0=no flexion response and 3=severe flexion response) and fetlock joint effusion from 0 to 2 (0=no swelling and 2=severe swelling). All the horses in this study showed initially a mild to moderate lameness (1-2 out of 5), mild to moderate response to flexion test (1-2 out of 3) and moderate to severe joint effusion (1-2 out of 2). As a result, all horses had a very similar initial clinical score of 4-5 out of 10. Because the importance of each parameter was correlated with its impact, the sum of these 3 parameters was reckoned as the overall clinical severity score (0 to 10), with 0 corresponding to clinical soundness. The progress of the overall scores (compared to before the treatment) was translated in a positive evolution score ranging from 0 to 5: 0=severity score of 5 out of 10; 1=severity score of 4 out of 10; 2=severity score of 3 out of 10; 3=severity score of 2 out of 10; 4=severity score of 1 out of 10; and 5=return to clinical soundness or severity score of 0 out of 10. Severity scores were translated to evolution scores for easier interpretation of the data and a positive trend would therefore indicate a clinical improvement. Statistical analysis was performed based upon the clinical evolution scores.

i. Statistical Analysis

For data analysis in study 1, the average of the evolution scores at 6 and 12 weeks represented the early evolution score, and the average of the evolution scores at 6 and 12 months represented the late evolution score. The early and late evolution scores are compared between the group receiving both MSCs (either native or induced) and PRP and the group receiving only MSCs on the one hand or receiving only PRP on the other hand, using the Wilcoxon signed rank sum test at the 5% significance level. Furthermore, within the combined treatment (study 2), the chondrogenic-induced MSCs are compared with native MSCs only for the earliest evolution score (i.e. at 6 weeks) equally using the Wilcoxon signed rank sum test at the 5% significance level.

j. Isolation of Mesenchymal Stem Cells (MSCs)

The first spindle shaped cells were noticed after 17 days in culture and were isolated at 21 days at approximately 60% confluency.

k. Characterization and Chondrogenic Induction of MSCs

To initially characterize MSCs and confirm chondrogenic induction, we analyzed cell morphology by light microscopy utilizing HE and Crystal Violet staining. Biochemical induction was analyzed by measuring gene and protein expression of selected cell markers (glycosaminoglycan production, collagen type II (Col II), Ki67 p63, vimentin, major histocompatibility complex, aggrecan, cartilage oligomeric matrix protein) providing insight into the degree of chondrogenic-induction by real-time RT-PCR, Alcian Blue staining, Safranin O staining, immunocytochemistry and flow cytometry. Light microscopic analysis in conjunction with HE and Crystal Violet staining showed that native MSCs (FIGS. 13A & C) had a stellate/spindle-shaped morphology and displayed a propensity to grow in colonies, whereas MSCs induced into the chondrogenic lineage (FIGS. 13B & D) showed a more rectangular morphology. In addition, a few chondrocyte-like cells in lacune-like structures could be noticed after 3 days of culturing in the chondrogenic-inducing medium (FIG. 13D). Gene expression analysis confirmed the switch towards a chondrogenic phenotype, exhibiting increases in the levels of Col II, aggrecan (ACAN) and cartilage oligomeric matrix protein (COMP) in induced MSCs, compared to native MSCs (FIG.

14). Histological staining of the cells with both Alcian Blue and Safranin O confirmed the production of glycosaminoglycans in the chondrogenic-induced group (FIGS. 15B & D), whereas undifferentiated MSCs stained negative (FIGS. 15A & C).

Immunocytochemistry on cytospins revealed that most of the nuclei in the native MSC group were positive for the proliferation marker Ki67, whereas noticeably less nuclei stained positively in the chondrogenic-induced group (FIG. 16A). Moreover, native MSCs and chondrogenic-induced MSCs were both positive for Col II (FIG. 16B). Cytospin analysis further indicated that native and chondrogenic-induced MSCs were immunoreactive for vimentin (FIG. 16C), while p63 (FIG. 16D), which is a member of the p53 tumor suppressor gene family, was only detectable in chondrogenic-induced MSCs. Isotype (FIG. 16) and negative controls (data not shown) stained negative.

Figure 17:
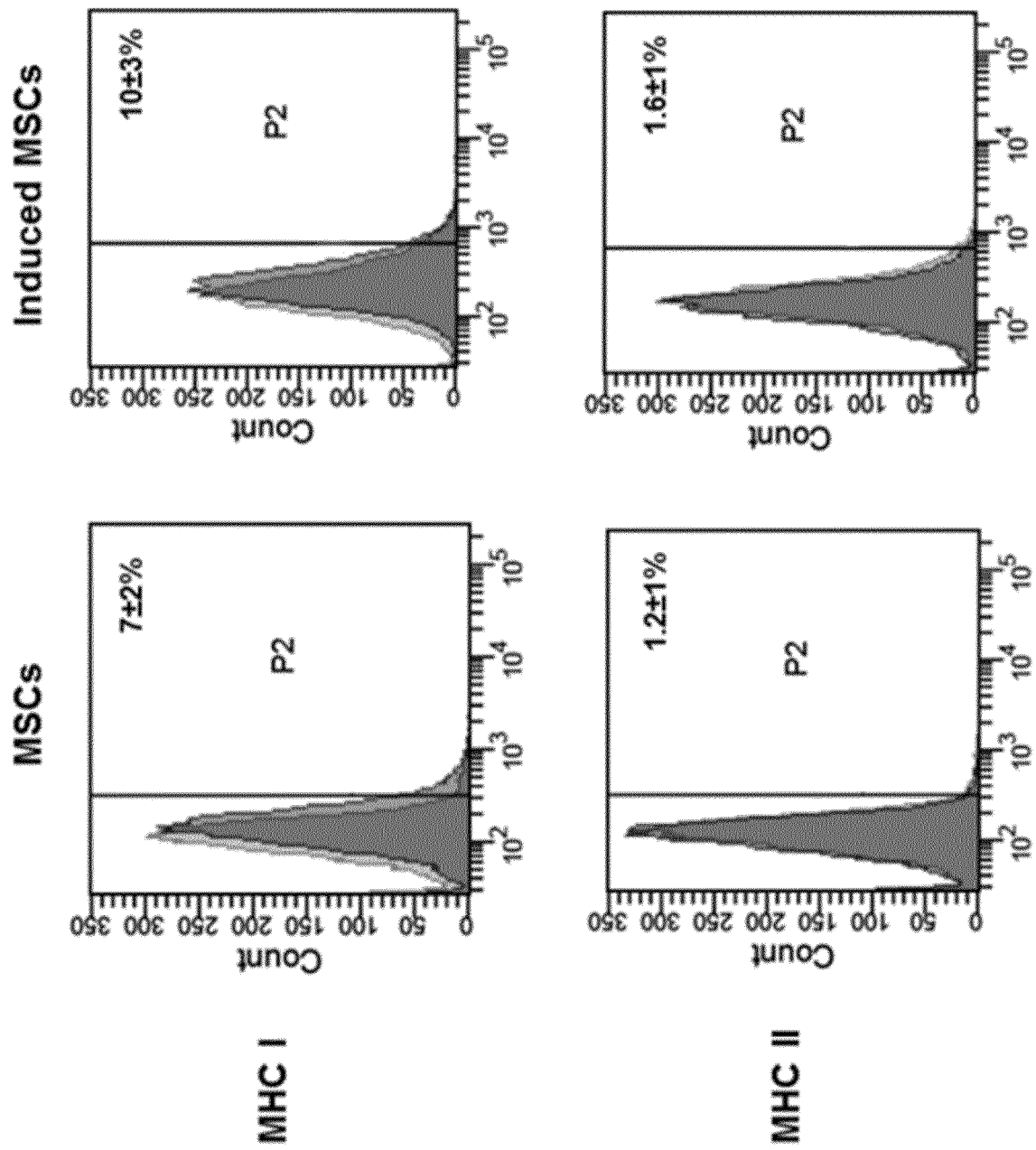
FIG. 17 shows flow cytometric experiments which confirmed a very low expression of major histocompatibility complex (MHC) class I and no expression of MHC class II on the native MSCs and chondrogenic induced MSCs. The light and dark grey histograms represent the relevant isotype control staining and marker antibody staining, respectively with the corresponding percentage of mean positive cells (gated as P2)±SEM.

In vitro differentiation towards undesired lineages (i.e. myogenic, endothelial, or smooth muscle differentiation) results in an increase of the expression of the major histocompatibility complex (MHC) classes I and II [Huang et al., 2010]. It is thus of relevance that our differentiation protocol showed no increase in these markers. While MHC class II expression was completely absent in both native and chondrogenic-induced MSCs (P=0.4), MHC class I was expressed in both types of MSCs (P=0.1), but at very low levels (FIGS. 17A & B).

I. Scoring of the clinical lameness

Study 1

Figure 18:
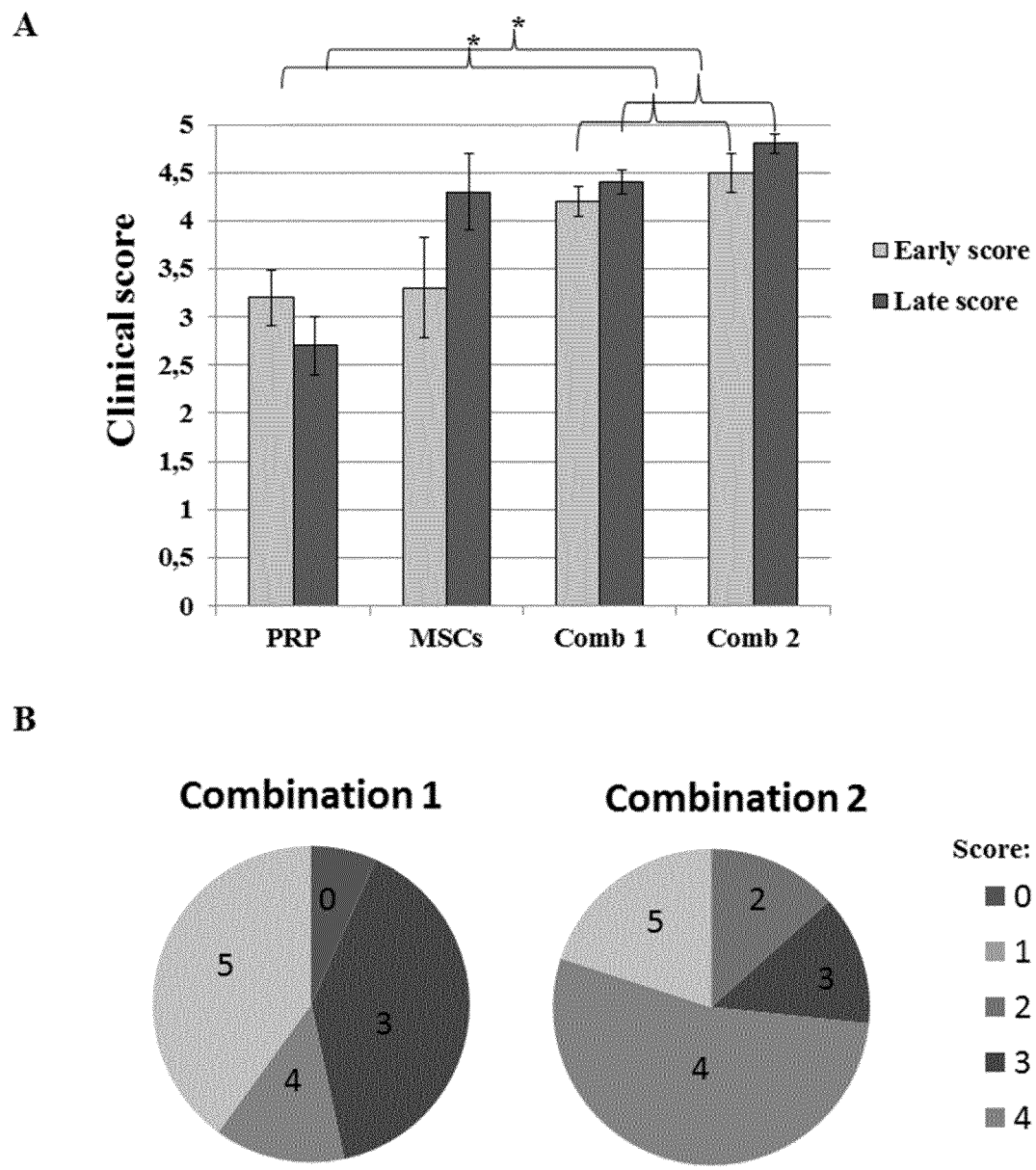
FIG. 18 shows the Clinical evolution scores of the different treatments at the early and late time point in the first study (A). Values are given as the mean±SEM. Diagrams represent the clinical evolution scores of 30 horses treated with native mesenchymal stem cells (MSCs) and platelet-rich plasma (PRP) (Combination 1, n=15) or chondrogenic induced MSCs and PRP (Combination 2, n=15) in the second study (B).

The clinical evolution score of each patient per treatment group can be found in Table 4. For the first study, an overview of the average evolution scores after each treatment is presented in FIG. 18A. The results of the different treatments with respect to the early and late evolution scores can be found in Table 5. The combined treatments were significantly better than the PRP treatment alone, both for the early evolution score (P=0.033) and the late evolution score (P=0.012). No significant differences were found between the combined treatment and the MSC treatment alone. The combined use of chondrogenic-induced MSCs and PRP generated the highest evolution scores, although the difference was not significantly higher than the combined use of native MSCs and PRP for either the early (P=0.530) or late evolution score (P=0.207).

TABLE 4

Clinical evolution scores for the different treatment groups with average and standard deviation (STD) at different time points.

| | | 6 weeks | 12 weeks | 6 months | 12 months |
|---|---|---|---|---|---|
| GROUP 1 | Horse 1 | 4 | 2 | 2 | 1 |
| | Horse 2 | 4 | 5 | 4 | 4 |
| | Horse 3 | 3 | 3 | 3 | 3 |
| | Horse 4 | 3 | 2 | 2 | 2 |
| | Horse 5 | 3 | 3 | 3 | 3 |
| | Average | 3.4 | 3 | 2.8 | 2.6 |
| GROUP 2 | Horse 6 | 3 | 4 | 5 | 5 |
| | Horse 7 | 0 | 1 | 2 | 2 |
| | Horse 8 | 3 | 4 | 5 | 5 |
| | Horse 9 | 4 | 4 | 5 | 4 |
| | Horse 10 | 5 | 5 | 5 | 5 |
| | Average | 3 | 3.6 | 4.4 | 4.2 |
| GROUP 3 | Horse 11 | 3 | 4 | 4 | 5 |
| | Horse 12 | 4 | 5 | 5 | 3 |
| | Horse 13 | 4 | 5 | 5 | 4 |
| | Horse 14 | 5 | 5 | 5 | 5 |
| | Horse 15 | 3 | 4 | 4 | 4 |
| | Average | 3.8 | 4.6 | 4.6 | 4.2 |
| GROUP 4 | Horse 16 | 4 | 4 | 5 | 5 |

TABLE 4-continued

Clinical evolution scores for the different treatment groups with average and standard deviation (STD) at different time points.

| | 6 weeks | 12 weeks | 6 months | 12 months |
|---|---|---|---|---|
| Horse 17 | 5 | 5 | 5 | 5 |
| Horse 18 | 4 | 4 | 4 | 4 |
| Horse 19 | 5 | 5 | 5 | 5 |
| Horse 20 | 4 | 5 | 5 | 5 |
| Average | 4.4 | 4.6 | 4.8 | 4.8 |

TABLE 5

Median, minimum (min) and maximum (max) of the early and late evolution score are indicated per treatment: platelet-rich plasma (PRP), native mesenchymal stem cells (MSCs), combination (Comb) 1 (native MSCs and PRP) or Comb 2 (chondrogenic induced MSCs)

| Treatment | Early score median (min; max) | Late score median (min; max) |
|---|---|---|
| PRP | 3.0 (2.5; 4.5) | 3.0 (1.5; 4.0) |
| MSCs | 3.5 (0.5; 5.0) | 5.0 (2.0; 5.0) |
| Comb 1 | 4.5 (3.5; 5.0) | 4.5 (4.0; 5.0) |
| Comb 2 | 4.5 (4.0; 5.0) | 5.0 (4.0; 5.0) |

Study 2

The second clinical study was performed in which a total of 30 horses were treated with either native MSCs plus PRP (Combination 1, n=15) or with chondrogenic-induced MSCs plus PRP (Combination 2, n=15). The horses were only evaluated at the first time point (i.e. 6 weeks post injection). Our results show that 53% (8/15) of the horses in the first group received an evolution score 4 or more, versus 73% (11/15) in the second group. However, in both treatment groups the average evolution score was approximately the same (3.7 vs 3.8) and no statistically significant (P=0.67) difference could be noticed (Table 6, FIG. 18B).

TABLE 6

Clinical evolution scores at 6 weeks after treatment of 15 horses with native mesenchymal stem cells (MSCs) and PRP (Combination 1) or chondrogenic induced MSCs and PRP

| | Combination 1 | Combination 2 |
|---|---|---|
| Horse 1 | 3 | 3 |
| Horse 2 | 5 | 4 |
| Horse 3 | 4 | 4 |
| Horse 4 | 4 | 4 |
| Horse 5 | 3 | 3 |
| Horse 6 | 5 | 4 |
| Horse 7 | 5 | 4 |
| Horse 8 | 3 | 5 |
| Horse 9 | 5 | 4 |
| Horse 10 | 3 | 5 |
| Horse 11 | 3 | 4 |
| Horse 12 | 0 | 2 |
| Horse 13 | 5 | 5 |
| Horse 14 | 5 | 4 |
| Horse 15 | 3 | 2 |
| Average | 3.7 | 3.8 |

The results indicate that chondrogenic induction can be achieved in equine MSCs and that the combined use of PRP and MSCs (chondrogenic induced or not) significantly improved the functionality and sustainability of damaged joints in horses with mild to moderate lameness, due to fetlock joint osteoarthritis, up to 12 months post treatment. The highest clinical scores were noticed upon treatment with the chondrogenic induced MSCs and PRP.

What is claimed is:

1. A method for inducing tenogenesis in isolated blood mesenchymal stem cells (MSCs), comprising culturing the MSCs in an inducing cell medium for a period of between 1 and 7 days to produce a population of tenogenic-induced cells, wherein said cell medium comprises a glucose medium supplemented with at least one growth factor, and wherein said growth factor is selected from fibroblast growth factors (FGF) or transforming growth factors (TGF), wherein said total FGF or total TGF is present in a concentration of between 1 and 15 ng/ml, and wherein said tenogenic-induced cells show an increase in collagen I expression of at least one and a half-fold and an increase in collagen III expression of at least eight-fold and a decrease in collagen II expression within a time span of 1 to 7 days, compared to non-induced cells.

2. The method according to claim 1, wherein said medium comprises 5 ng/ml FGF-2.

3. The method according to claim 1, wherein said MSCs are mammalian derived.

4. A method for inducing tenogenesis in isolated blood mesenchymal stem cells (MSCs), comprising:
culturing said MSCs in an inducing cell medium for a period of between 1 and 7 days to produce a population of tenogenic-induced cells,
wherein said medium comprises a glucose medium supplemented with at least one growth factor selected from the group consisting of a fibroblast growth factor (FGF) and a transforming growth factor (TGF),
wherein said FGF is selected from the group consisting of FGF-1, FGF-2, FGF-3, FGF-4, FGF-5, FGF-6, FGF-7, FGF-8, FGF-9, FGF-10, and combinations thereof,
wherein said TGF is selected from the group consisting of TGFα, TGFβ1, TGFβ2, TGFβ3, and combinations thereof,
wherein said total FGF, or total TGF, is present in a total concentration of between 1 and 15 ng/ml in said inducing cell medium, and
wherein said tenogenic-induced cells show an increase in collagen I expression of at least one and a half-fold and an increase in collagen III expression of at least eight-fold, and a decrease in collagen II expression, within a time span of 1 to 7 days as compared to non-induced cells.

5. The method according to claim 4, wherein said total FGF or total TGF is present in a concentration of between 2 and 10 ng/ml.

6. The method according to claim 4, wherein said medium further comprises insulin-like growth factor (IGF), selected from the group consisting of IGF-1, IGF-2, IGF-I, and combinations thereof in a concentration of between 10 and 225 ng/ml.

7. The method according to claim 4, wherein said MSCs are seeded at a density of 2 to $30 \times 10^3$ MSCs/cm$^2$.

8. The method according to claim 4, wherein said mesenchymal stem cells are isolated from mammalian blood.

* * * * *

UNITED STATES PATENT AND TRADEMARK OFFICE
CERTIFICATE OF CORRECTION

PATENT NO. : 10,801,014 B2
APPLICATION NO. : 15/038172
DATED : October 13, 2020
INVENTOR(S) : Broeckx et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 321 days.

Signed and Sealed this
Thirty-first Day of January, 2023

Katherine Kelly Vidal
*Director of the United States Patent and Trademark Office*